United States Patent
Campbell

(10) Patent No.: US 12,121,351 B1
(45) Date of Patent: Oct. 22, 2024

(54) PLUGGABLE DISTAL MEASUREMENT INTERFACE

(71) Applicant: Airware, Inc., Newbury Park, CA (US)

(72) Inventor: Thomas G Campbell, Newbury Park, CA (US)

(73) Assignee: AIRWARE, INC., Newbury Park, CA (US)

( * ) Notice: Subject to any disclaimer, the term of this patent is extended or adjusted under 35 U.S.C. 154(b) by 531 days.

(21) Appl. No.: 17/320,601

(22) Filed: May 14, 2021

Related U.S. Application Data

(60) Provisional application No. 63/137,977, filed on Jan. 15, 2021.

(51) Int. Cl.
| | | |
|---|---|---|
| A61B 5/1455 | (2006.01) | |
| A61B 5/00 | (2006.01) | |
| A61B 5/145 | (2006.01) | |

(52) U.S. Cl.
CPC ........ *A61B 5/1455* (2013.01); *A61B 5/14546* (2013.01); *A61B 5/6816* (2013.01); *A61B 5/6819* (2013.01); *A61B 5/6825* (2013.01); *A61B 5/6838* (2013.01); *A61B 5/742* (2013.01); *A61B 5/14532* (2013.01)

(58) Field of Classification Search
CPC . A61B 5/0205; A61B 5/1455; A61B 5/14551; A61B 5/14546; A61B 5/14532; A61B 5/6816; A61B 5/6819; A61B 5/6825; A61B 5/6838
See application file for complete search history.

(56) References Cited

U.S. PATENT DOCUMENTS

| | | | |
|---|---|---|---|
| 6,095,974 A * | 8/2000 | Shemwell | A61B 5/6826 600/323 |
| 6,285,894 B1 * | 9/2001 | Oppelt | A61B 5/1455 600/335 |
| 8,073,518 B2 | 12/2011 | Chi | |
| 8,700,116 B2 | 4/2014 | Schlottau et al. | |
| 8,798,703 B2 | 8/2014 | Huber et al. | |
| 8,965,473 B2 | 2/2015 | Hoarau et al. | |
| 9,254,087 B2 | 2/2016 | Isaacson et al. | |
| 9,606,053 B1 | 3/2017 | Wong et al. | |
| 9,678,000 B1 | 6/2017 | Wong et al. | |
| 9,717,458 B2 | 8/2017 | Lamego et al. | |
| 9,726,601 B1 | 8/2017 | Wong et al. | |
| 9,823,185 B1 | 11/2017 | Wong et al. | |
| 10,041,881 B2 | 8/2018 | Wong et al. | |

(Continued)

*Primary Examiner* — Chu Chuan Liu
(74) *Attorney, Agent, or Firm* — Roy L. Anderson

(57) ABSTRACT

A controller and a distal sensor module are used to emit optical emissions to a liquid sample being tested in a human body and detect desired optical data which the controller uses to electronically calculate a concentration measurement of a targeted analyte (e.g., glucose). The distal sensor module is held in place by a retention mechanism while a clamping system applies clamping pressure to the liquid sample during a test period to maintain a specified sample height of the liquid sample. An optical cable is intermediate the controller and the distal sensor module and is pluggably connected to the controller. Continuous monitoring of the analyte is possible without disconnecting the controller from the optical cable or the distal sensor module from the patient while clamping pressure on the test sample is reduced outside of the test period.

16 Claims, 24 Drawing Sheets

(56) References Cited

U.S. PATENT DOCUMENTS 10,241,044 B2 3/2019 Wong et al.
10,473,586 B2 11/2019 Campbell et al.
2002/0165439 A1* 11/2002 Schmitt ................ A61B 5/6838
600/320

* cited by examiner

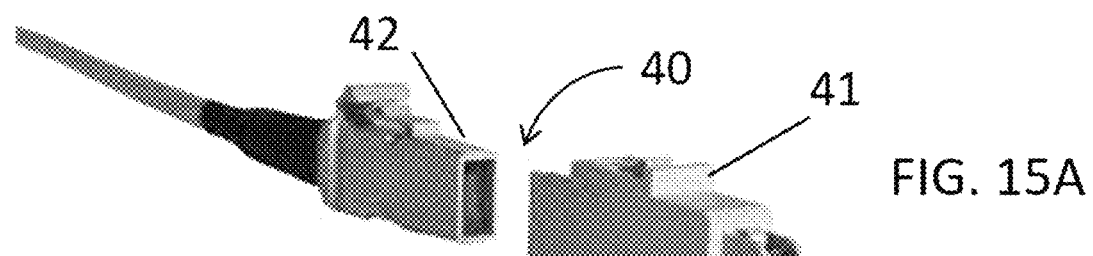
FIG. 15A
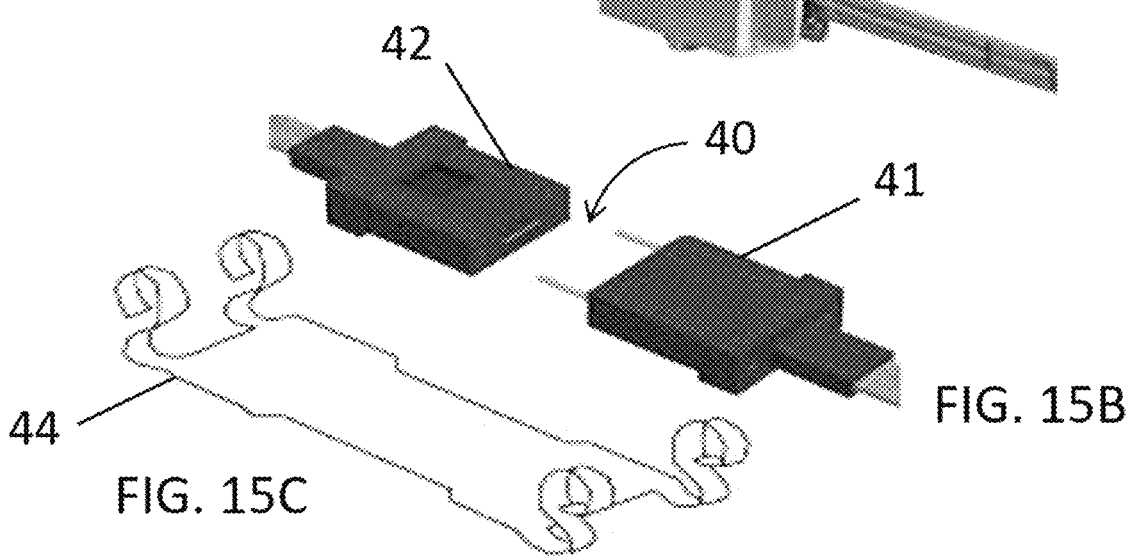
FIG. 15B
FIG. 15C
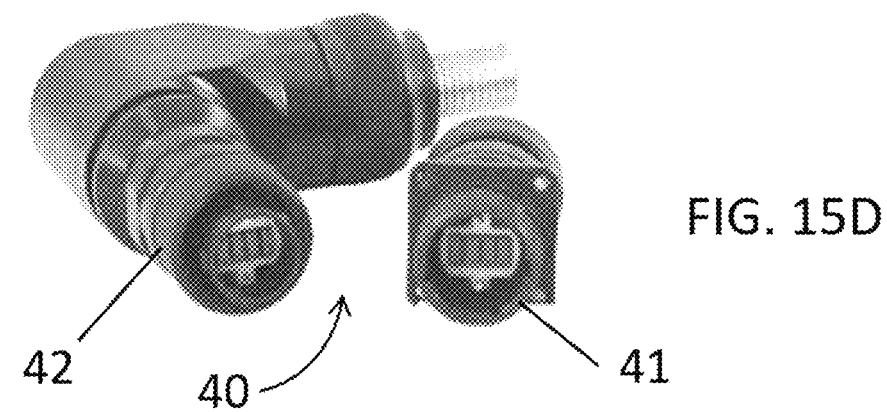
FIG. 15D

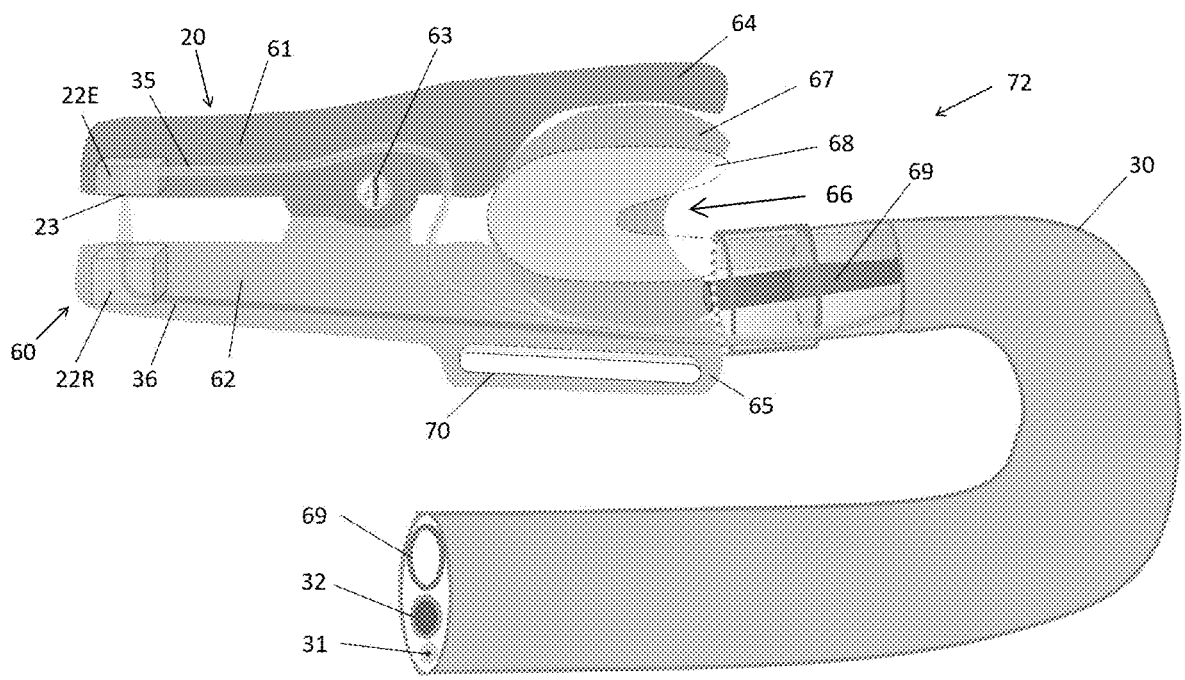
FIG. 17A
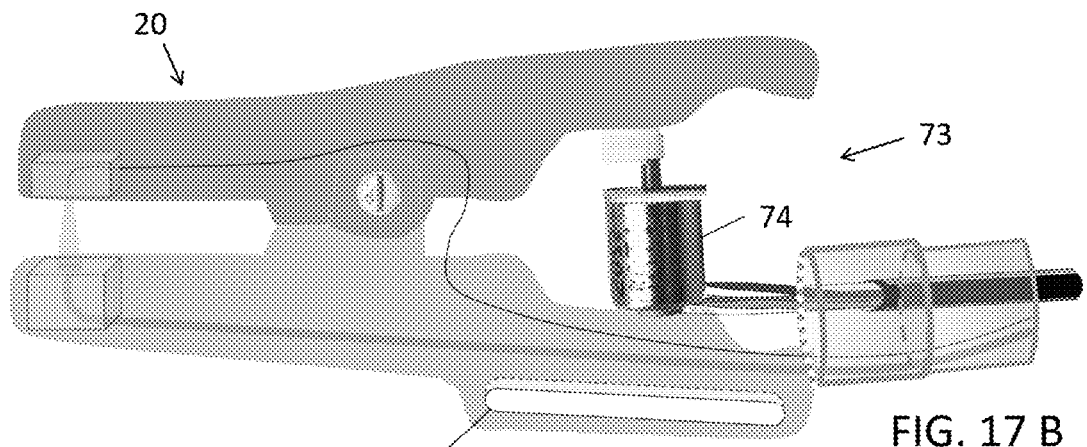
FIG. 17 B
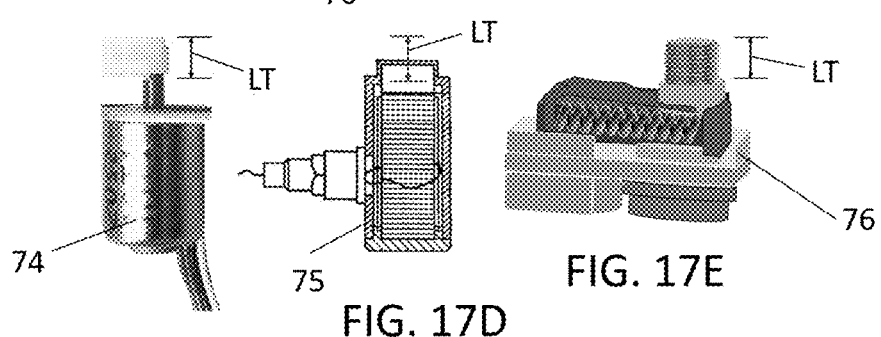
FIG. 17 C
FIG. 17D
FIG. 17E

PLUGGABLE DISTAL MEASUREMENT INTERFACE

CROSS REFERENCE TO RELATED APPLICATIONS

This application is a non-provisional application which claims priority from U.S. Ser. No. 63/137,977, filed Jan. 15, 2021, the disclosure of which is specifically incorporated by reference herein in its entirety.

FIELD OF THE INVENTION

The present invention relates generally to a pluggable distal measurement device and, more particularly, to one that can be used to non-invasively measure the concentration of glucose and other human and chemical analytes in a human patient.

BACKGROUND OF THE INVENTION

Measuring glucose in patients and persons with diabetes or pre-diabetes is an important and widespread problem, and billions of dollars have spent in this field over several decades.

Recently, pioneering break-through methods for measuring blood glucose non-invasively have been disclosed in U.S. Pat. Nos. 9,606,053; 9,678,000; 9,726,601; 9,823,185; 10,041,881; 10,241,044; and 10,473,586, the disclosures of all of which are specifically incorporated herein by reference in their entireties.

The present invention advances devices and methods useful for applying such pioneering methods to non-invasively measure glucose in patients, including the special case of continuous monitoring in a controlled setting, such as where humans receive care in hospitals or other acute or chronic care facilities.

SUMMARY OF THE INVENTION

The present invention is generally directed to an apparatus and its use in which a controller is configured to deliver controlled optical emissions to a liquid sample being tested in a human body, to capture desired optical data returned from the liquid sample, and to electronically calculate a concentration measurement of a targeted analyte (e.g., glucose) in the liquid sample through use of a preselected algorithm with the captured optical data; a distal sensor module is configured to be held in place by a retention mechanism, to deliver controlled optical emissions to the liquid sample, and then to capture optical effects from the liquid sample; a clamping system is configured to apply clamping pressure to the liquid sample to maintain a specified sample height of the liquid sample during a test period; an optical cable is configured to transmit controlled optical emissions from the controller to the distal sensor module and then to return captured optical effects from the distal sensor module to the controller; a connector system (which can be pluggable) is configured to allow the distal sensor module to be connected to and disconnected from the controller; and an information interface is configured to output the concentration measurement.

The distal sensor can be configured to apply a first clamping pressure sufficient to maintain the distal sensor module clamped to the human body and apply a second clamping pressure to maintain the specified sample height of the liquid sample during the test period, the second clamping pressure being greater than the first clamping pressure, and the second clamping pressure need only be applied during a preselected time frame which includes a sample time period during the test period. A clamping system can generate the necessary clamping force by pneumatic-mechanical clamping means, electro-mechanical clamping means or apply a preselected clamping pressure.

The distal sensor can use at least one optical fiber emitter and at least one optical fiber receiver, which can be single mode optical fibers or multimode optical fibers, and emitter and receiver optical elements can be used, while a second distal sensor module can be used with the controller to calculate a second concentration measurement of the targeted analyte.

In use, once the distal sensor is plugged into the controller and clamped to the human patient, and the liquid sample with a specified sample height is established by mechanical means during a test period, optical emissions are transmitted into the liquid sample and optical effects are captured during the test period, and then pressure on the liquid sample can be reduced after the test period while the distal sensor remains attached to the human body and connected to the remote controller, thus allowing the process to be repeated without detaching the distal sensor from the controller or removing it from the human body.

Accordingly, an object of the present invention is to provide a pluggable distal measurement device capable of being used to non-invasively measure the concentration of glucose in a human patient.

This and further objects and advantages will be apparent to those skilled in the art in connection with the figures and the detailed description of the invention set forth below.

BRIEF DESCRIPTION OF THE FIGURES

FIGS. 2A-2C illustrate three single mode fibers used as an optical fiber emitter, FIG. 2A being a side view, FIG. 2B being an end view and FIG. 2C being a sample interface view, while

FIG. 7 illustrates an anti-reflective coating and a ball lens used with a formed single mode optical fiber as optical fiber emitter while

FIG. 9 illustrates three single mode optical formed fibers aligned in an emitter block along with the use of anti-reflective coatings and emitter ball lenses while

FIGS. 15A, 15B and 15D illustrate examples of pluggable connector systems useful with the present invention while FIG. 15C illustrates one form of a retention means which is suitable for use with the pluggable system of FIG. 15B.

FIG. 17A illustrates a cross section of the distal sensor module of FIG. 16 rotated ninety degrees and illustrates use of pneumatic pressure to inflate a pressure bladder inside of the spring clamp. In FIG. 17B, a stepper motor is used inside of the same spring clamp to replace use of pneumatic pressure to inflate a pressure bladder. FIGS. 17C, D and E illustrate, respectively, a stepper motor, a linear piezo actuator and a linear piezo actuator with ratchet, all of which can be used inside of the spring clamp.

DETAILED DESCRIPTION OF THE INVENTION

Figure 1:
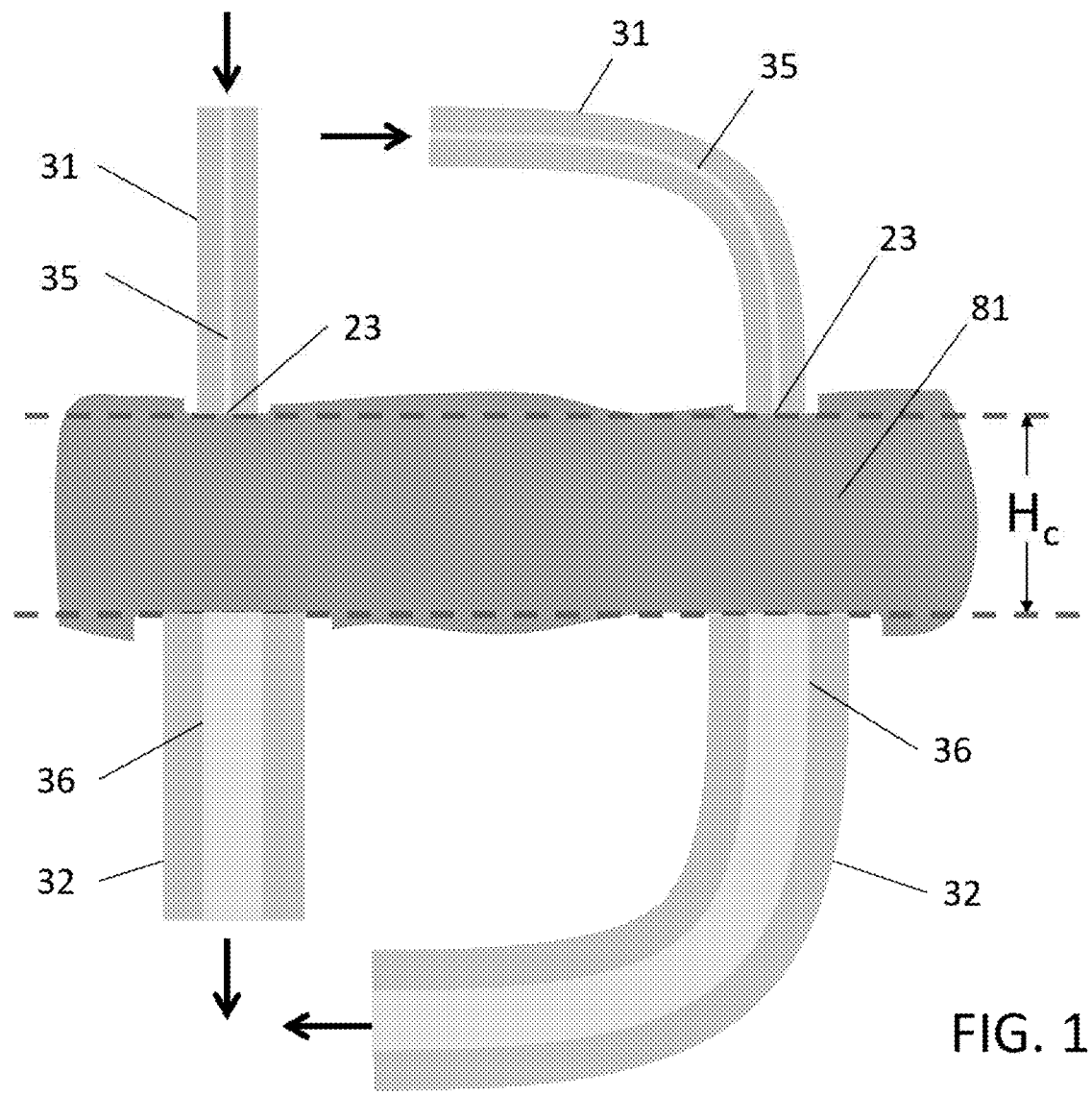
FIG. 1 illustrates both a straight and a formed design for optical fibers used in accordance with the present invention.
Figure 2A:
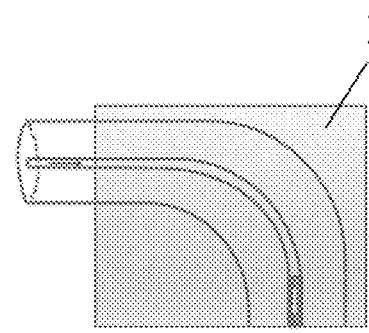
Figure 2B:
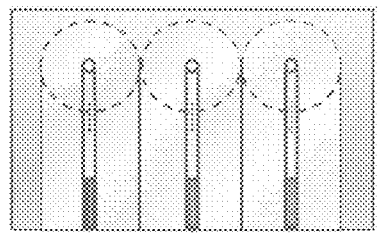
Figure 2C:
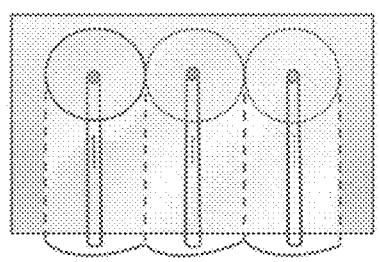
Figure 2E:
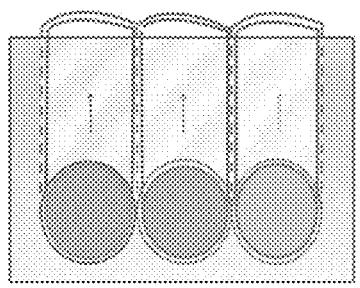
FIGS. 2D-2F illustrate three multi-mode fibers used as an optical fiber receiver, FIG. 2D being a side view, FIG. 2E being an end view and FIG. 2F being a sample interface view.
Figure 2D:
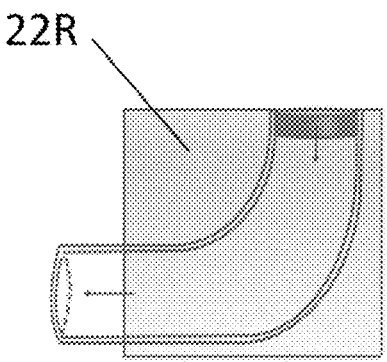
Figure 2F:
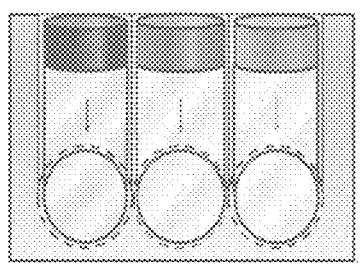

The present invention is generally directed to an optical measurement system especially well-suited for use with a human body (although it might also be used on animal bodies) which separates a controller, with its optical, electronic and software components, from a distal sensor module which comes into contact with the subject's body and is used to define a liquid sample within the subject's body. It is especially preferred that the sensor module be detachably connected to the controller, and an especially preferred manner of accomplishing this is to create a pluggable system which uses optical fibers for transmission of light between the controller and the distal sensor module (which may be permanently attached to, or integral with, the optical fibers). Finally, although it may find other applications, and it is not limited solely to a single application, the present invention is especially well-suited for use with an enhanced optical data capture using NDIR for liquids as is disclosed in U.S. Pat. No. 10,473,586.

Selection of a detachable distal sensor is especially useful in conditions where the measurement interface may become worn, degraded, or contaminated in some way, or when a single use (per testing subject) is required.

For a detachable distal sensor to be useful and viable, it must have a design which is robust, sufficiently sensitive in detection, and cost effective. The optical, electronic, and pneumatic connector interface should maintain the light delivery as required for implementation of an enhanced optical data capture using NDIR for liquids.

It is also especially desirable for a detachable distal sensor to apply sufficient and necessary pressure to maintain a specified fixed sampling height for consistent and highly accurate measurement of target analyte(s). (The fixed sampling height may include a fixed range, meaning it need not be a single measurement.) A clamping force (to maintain a specified fixed sampling height, as opposed to what might be referred to as clip pressure or retentive forces, such as clips, hooks, or straps, used to generally secure the distal measurement interface in relation to the test sample or patient being monitored) can be generated by any number of mechanical means, including pneumatic-mechanical clamping means and electro-mechanical clamping means. Some exemplary examples of mechanical means include, but are not limited to, spring(s), elastomeric structure(s), a pneumatic system, while some exemplary examples of electromechanical means include, but are not limited to, stepper motors and piezo elements or solenoid types of devices that make use of electromotive forces. It is especially preferred that the clamping force need only be applied during the actual measurement period, or a little larger period of time which includes the test period.

Because the present invention proposes separating the controller from the distal sensor module, high-cost elements can be included in the controller, which is reusable. Such high-cost elements may include narrow band laser emitters which are part of a light emitter system, one or more detectors which are part of a light detection system and electronics configured to use a preselected algorithm (such as is taught in U.S. Pat. Nos. 10,041,881 and 10,241,044). The controller may include a mechanical housing that is suspended from or mounts to a mobile cart or stand which allows it to be located adjacent to a patient's bed (i.e., a bedside controller) or a mechanical housing that is transportable, but designed to sit on a table top (i.e., a table top controller), and it will include electronics that comprise emitter circuitry, detector circuitry, processing electronics, a display interface with user input controls, and operating software.

The controller is optically connected to the distal measurement interface of the distal sensor module by fiber optics which have relatively low loss characteristics that make fiber optics uniquely suited for use in the present invention; however, certain optical components may be required to enhance the function of the optical fibers delivering the controlled optical emissions and capturing the optical effects of such optical emissions on the sample being tested. A connector system is used to physically and mechanically connect and disconnect the distal sensor module with the controller, and it is especially preferred that the connector system be a pluggable system having two or more parts that can be plugged into and unplugged from each other.

The invention will now be described in even greater detail by reference to especially preferred embodiments illustrated in FIGS. 1-24. In the Figures and the following description, number designations indicate various features of the invention, with like number designations referring to like features throughout both the drawings and the description. Although the Figures are described in greater detail below, the following is a glossary of the elements identified in the Figures.

Figure 23:
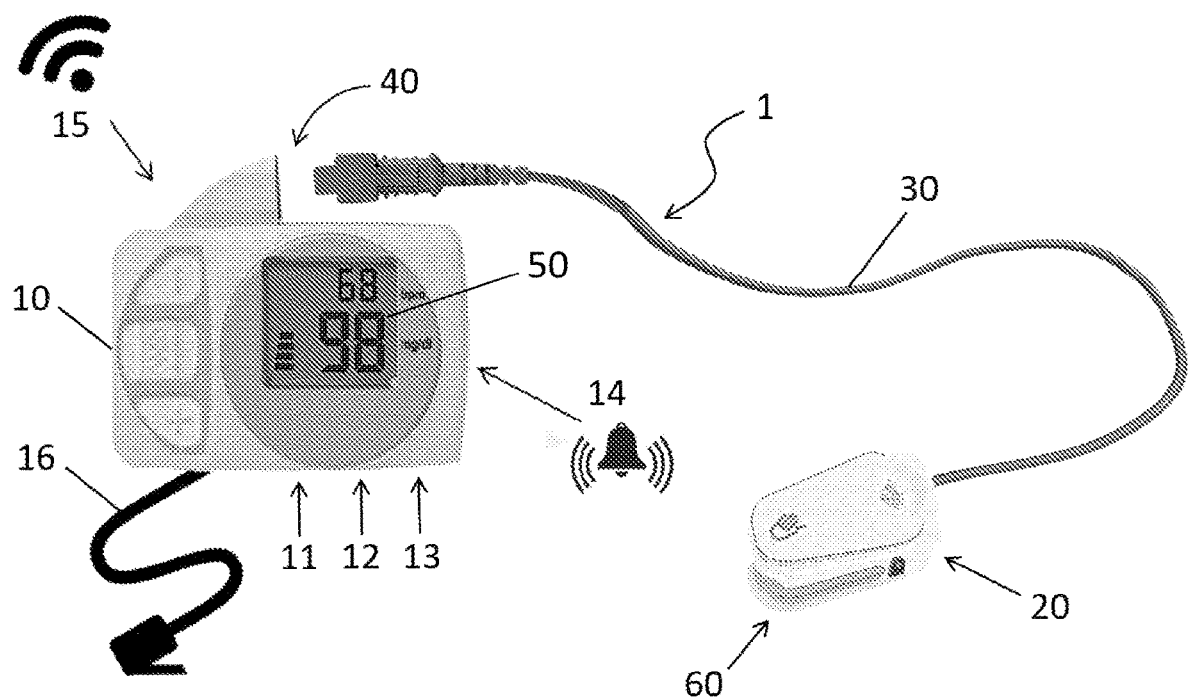
FIG. 23 illustrates an apparatus in accordance with the present invention.

1 apparatus
10 controller
11 light emitter system
12 light detection system
13 electronics 14 auditory alarm
15 wireless communication
16 wired communication
20 distal sensor module
21 retention mechanism
22 block (for mounting one or more optical fibers)
22E emitter block
22R receiver block
23 emission point
25 anti-reflective coating
28 alignment means
30 optical cable
31 single mode optical fiber
32 multimode optical fiber
33 emitter optical element
33B emitter ball lens
33P emitter prism
34 receiver optical element
34P receiver prism
34R receiver reflector
35 optical fiber emitter
36 optical fiber receiver
37 stranded electrical conductor
38 braided shielding around electrical conductors
39 cable jacket
40 connector system
41 one half of a pluggable connector system 40
42 a second half of a pluggable connector system 40
44 connector retention means
50 information interface system
60 clamping system
61 clamp jaw
62 clamp jaw
63 spring
64 handle
65 handle
66 pressure bladder
67 pressure bladder at inflated pressure
68 pressure bladder at deflated pressure
69 pneumatic line
70 slot for thumb strap
71 thumb strap
72 pneumatic-mechanical clamping means
73 electro-mechanical clamping means
74 stepper motor
75 linear piezo actuator
76 linear piezo actuator with ratchet
80 human sample site
81 liquid sample
90 human body
$H_c$ specified sample height
LT length of travel FIG. 23 illustrates one embodiment of an apparatus 1 in accordance with the present invention which has a controller, generally designated as 10, which is pluggably connected to a distal sensor module, generally designated 20, by a connector system, generally designated as 40. Controller 10 houses a light emitter system, generally designated as 11, a light detection system, generally designated as 12, and electronics, generally designated as 13. Controller 10 can include an auditory alarm 14, communicate wirelessly 15 or by a wired connection 16, and have an information interface system 50 configured to output information, such as a calculated concentration of a targeted analyte in a liquid sample 81 of a human body 90. In addition to buttons, switches, or touch pad interface, a bedside or table top controller 10 can display the appropriate measurement information which may include, but not be limited to, glucose concentration (mg/dl, mmol/L) that may be interstitial fluid related or blood sugar related; heart rate; temperature; pulse oximetry, blood pressure and hydration level (e.g., scale of 1-10, percent of water compared to total body mass). Controller 10 can also incorporate suitable alarms based on pre-set alarm levels, and alarm notifications may be conveyed audibly or by a wired or wireless communication reporting to a monitoring system or control point.

Distal sensor module 20 is configured to be held in place to a human body 90 by a retention mechanism, generally designated 21, such as a mechanical clamp or an adhesive mechanism (such as tape, glue and the like). Distal sensor module 20 also is configured with a clamping system, generally designated as 60, which is configured to apply clamping pressure to liquid sample 81 to maintain a specified sample height $H_c$ of liquid sample 81 during a test period. Distal sensor module 20 is configured so that at least one optical fiber emitter 35 maintains optical signal quality to the test zone and is aligned with at least one optical fiber receiver 36 which captures a high-quality signal from the test site exit zone with very low loss in the system. The at least one optical fiber emitter 35 and the at least one optical fiber receiver 36 are combined into a common cable design of optical cable 30 which is configured to transmit controlled optical emissions from controller 10 to distal sensor module 20 and then to return captured optical effects from digital sensor module 20 to controller 10 (and, if needed, to transmit electrical signals and pneumatics to and from controller 10 and distal sensor module 20).

One or more optical fibers will transmit optical signals from controller 10 to emission point 23 of distal sensor module 20, although it is especially preferred that a single mode optical fiber 31 be used for such transmission. In one preferred embodiment, a single mode optical fiber 31 can be mounted into a block 22 that is finished and polished exposing an interface surface as the emission point 23 as is illustrated in FIG. 1. Fibers may remain straight or can be formed in a design that permits particular desired dimensions for the sensor module, and FIG. 1 illustrates both options (although in an actual embodiment only one option would be selected). Multiple input fibers and multiple output fibers may be employed for enhanced data gathering, as is illustrated in FIGS. 2A-F, and a suitable mechanism can be used to step the couple laser pulses across multiple input fibers (e.g., an optical switch that employs linear or rotary elements to guide laser pulses to separate output fibers) for multi-site data averaging. Note that on the optical data return side, if multiple fibers are used, they can be directed to individual detectors, or coupled into a single input to a single detector.

Figure 3:
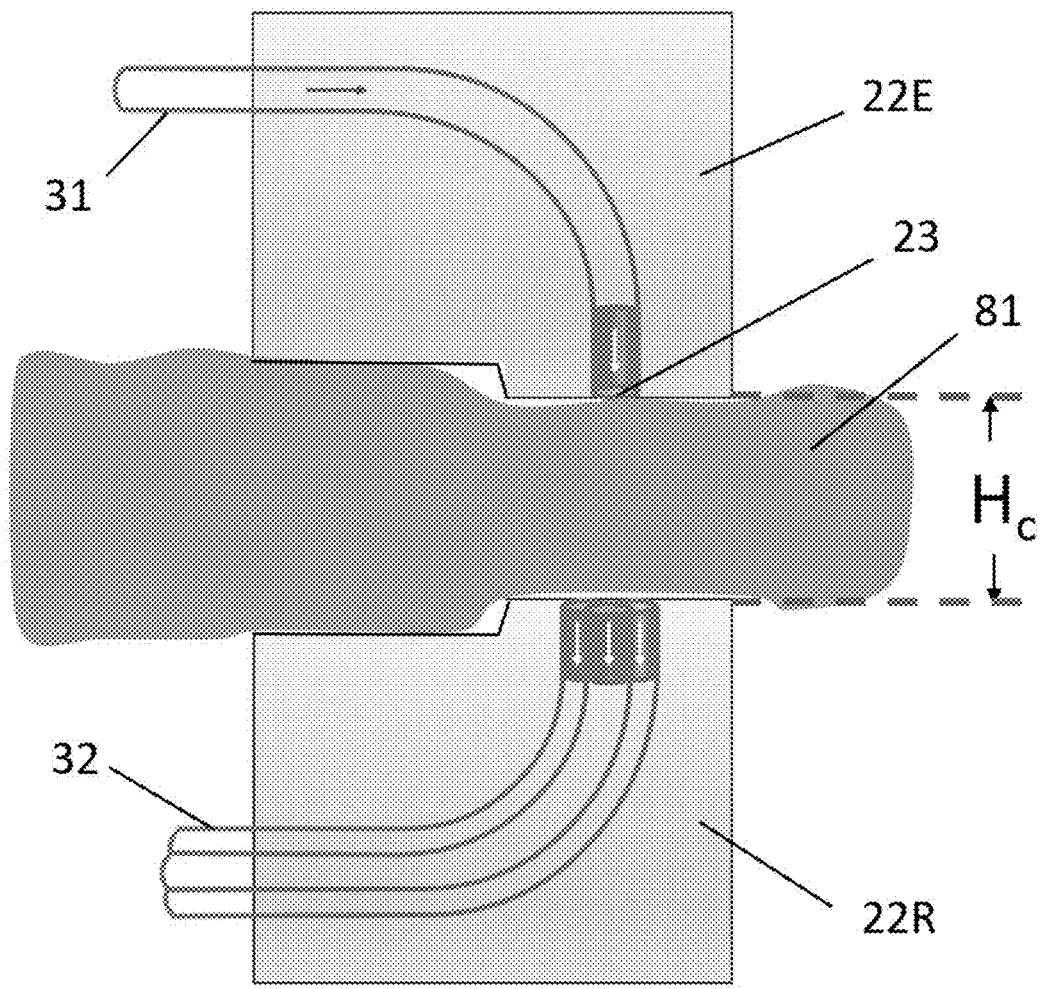
FIG. 3 illustrates a single optical emitter and a multimode optical receiver where the ends of the emitter and the receiver are cleaved and located in a housing to expose the cleaved surfaces as optical interfaces.

In another embodiment, the single mode optical fiber 31 or multimode optical fibers 32 can be cleaved and then located into a housing exposing a controlled surface, as is illustrated in FIG. 3.

Figure 4:
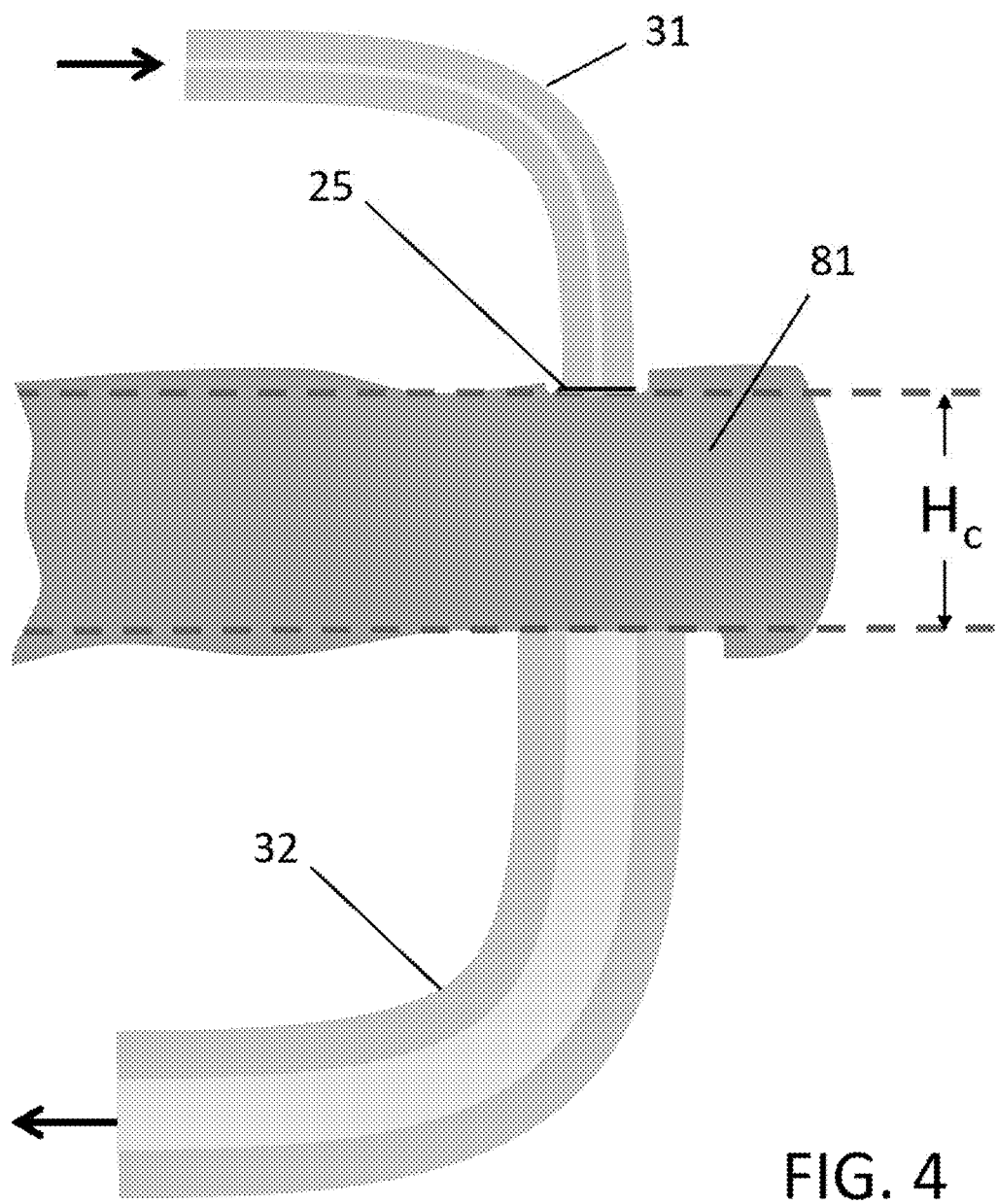
FIG. 4 illustrates use of an anti-reflective coating with a formed single optical emitter.
Figure 5:
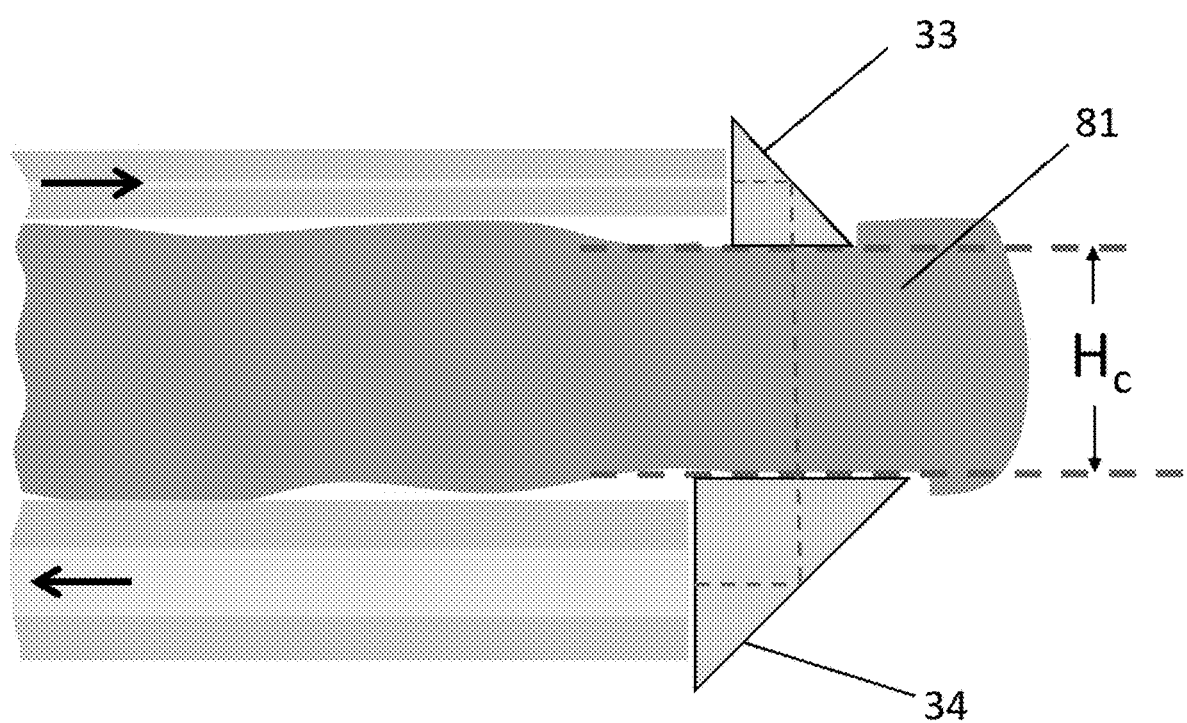
FIG. 5 illustrates use of emitter and receiver optical elements with unformed fiber with polished or cleaved ends.
Figure 6:
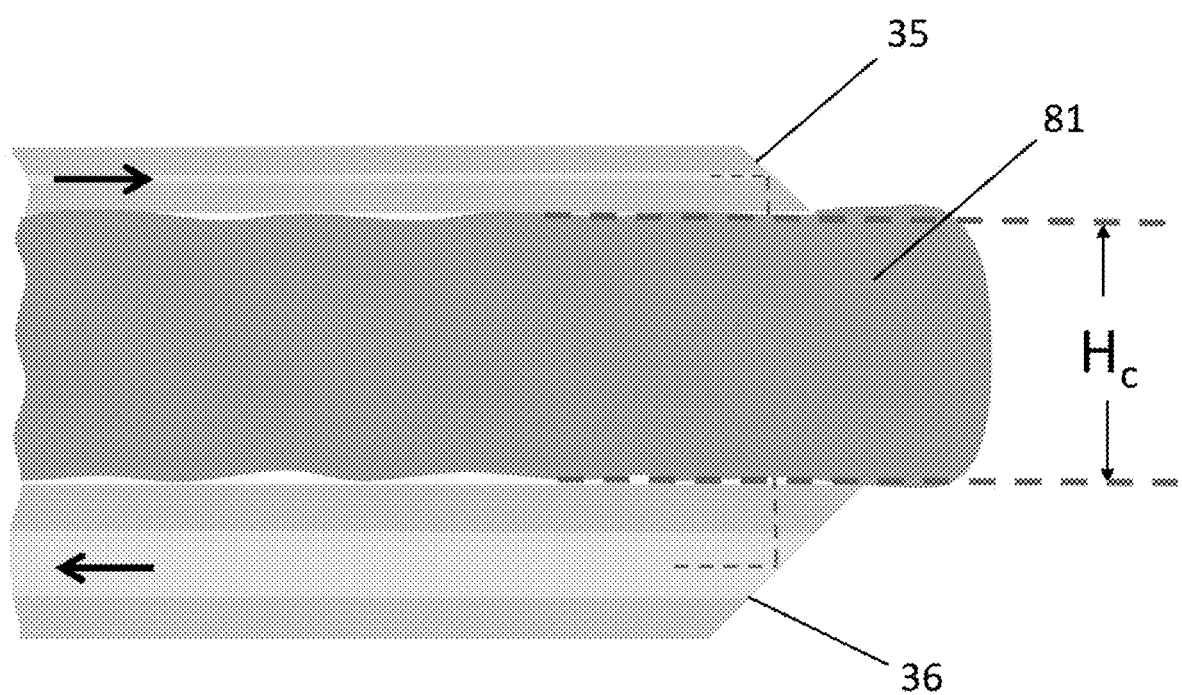
FIG. 6 illustrates use of unformed fibers with polished or cleaved ends in which the fiber ends are prepared for a ninety-degree emission (or optical devices can also be added, but are not shown).
Figure 7:
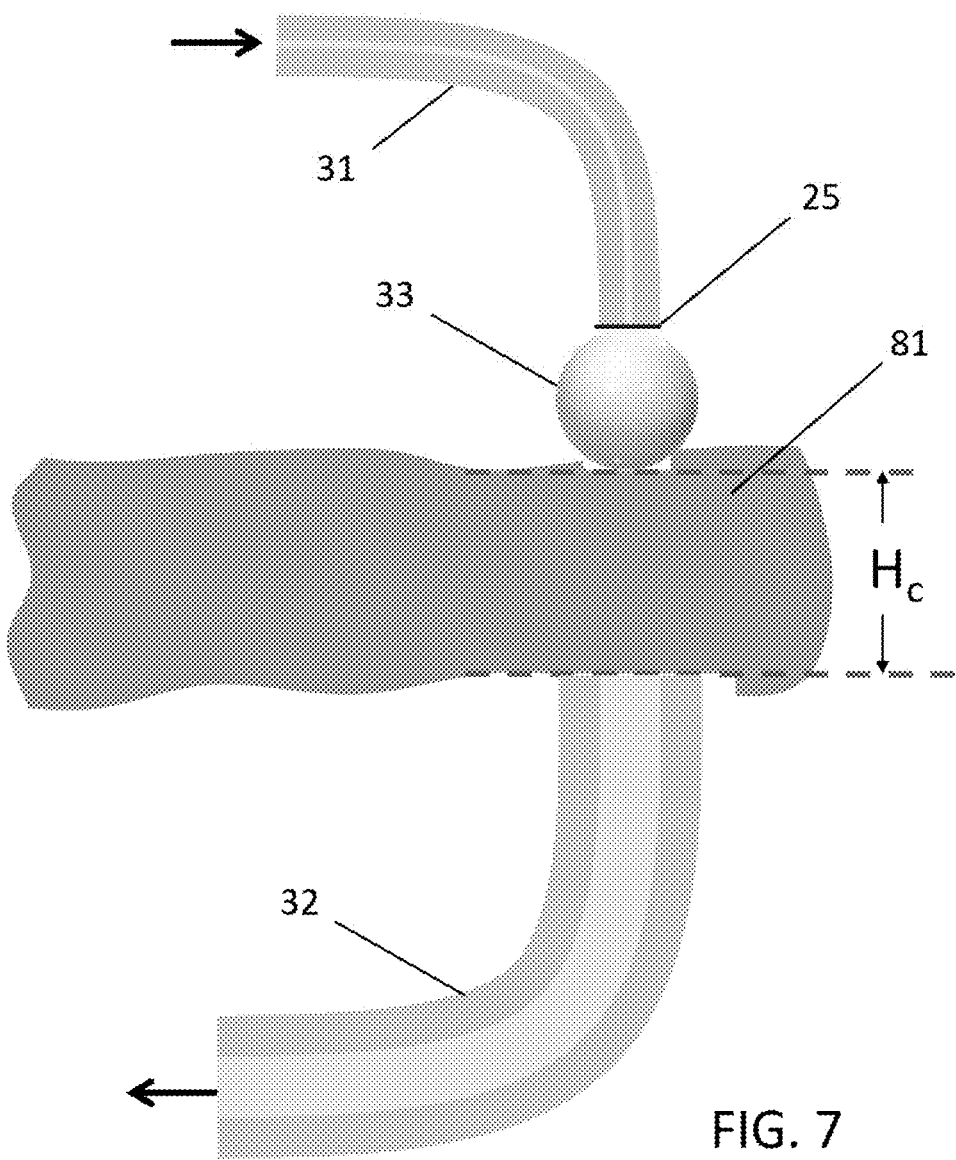
Figure 8:
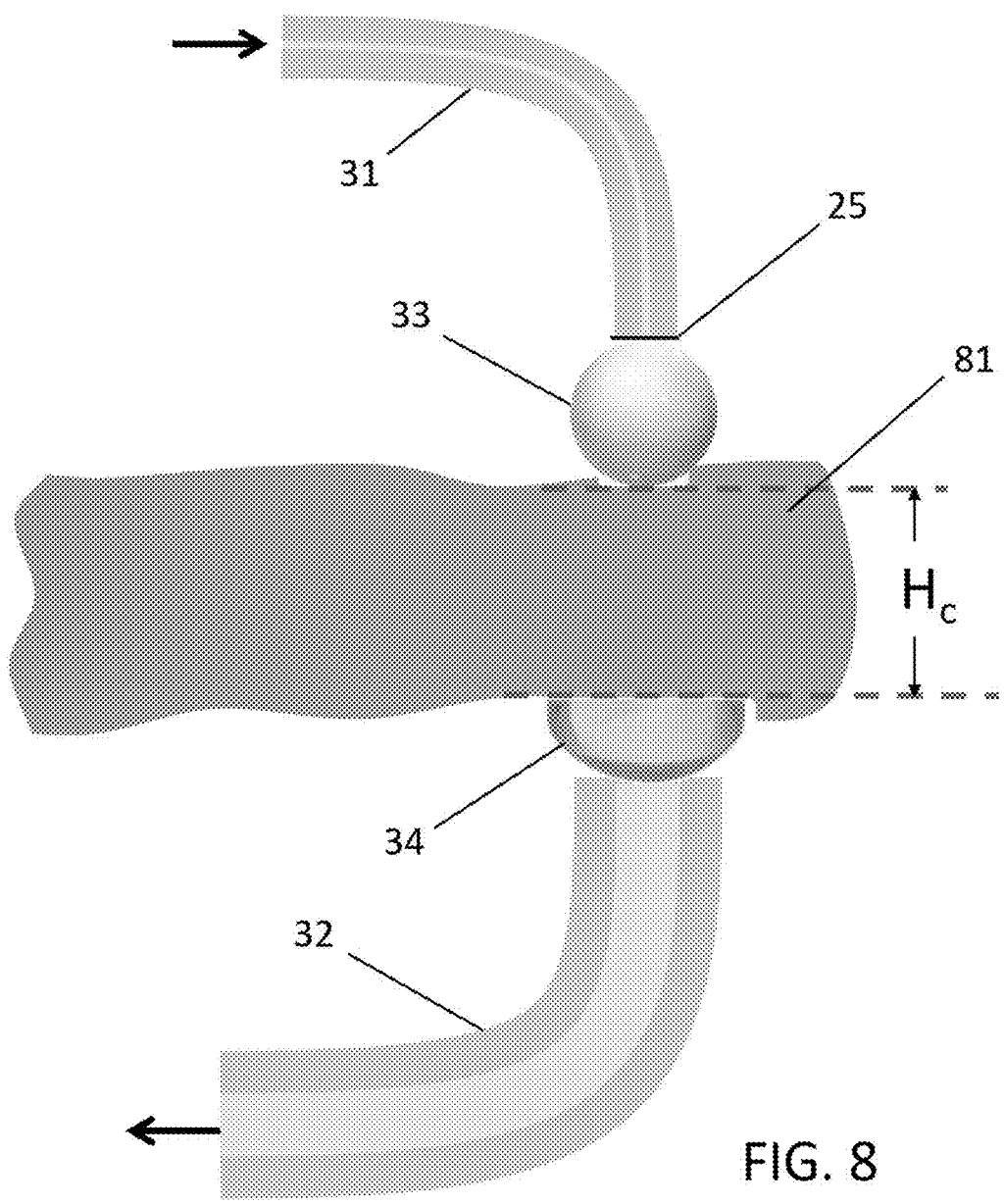
FIG. 8 illustrates the addition of a receiver optical element.

An anti-reflective coating 25 may be applied to the input optical fibers/lens assembly to minimize or eliminate reflected energy backwards to the optics and electronics, as is illustrated in FIG. 4. An anti-reflective coating 25 can take the embodiment of a deposited vapor, a liquid, a flexible film, or a rigid lens element.

Figure 9:
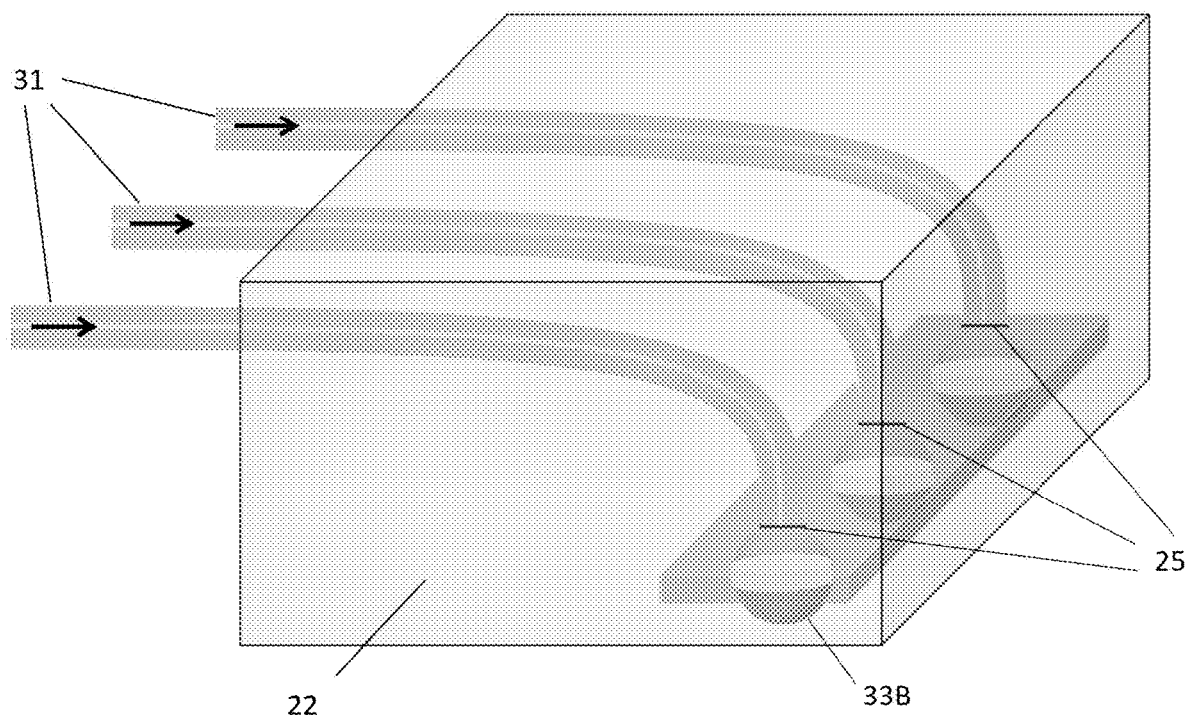
Figure 10:
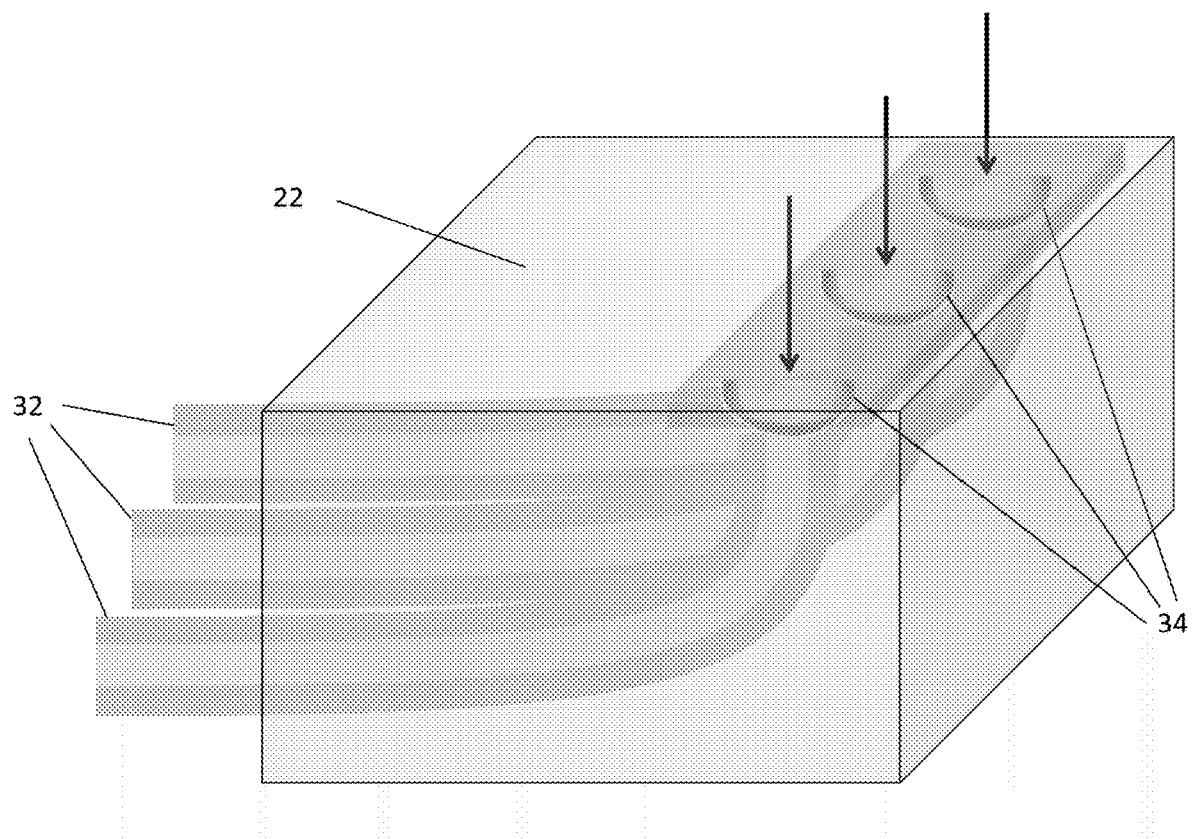
FIG. 10 illustrates three multimode formed fibers aligned in a receiver block with the use of receiver optical elements.
Figure 11:
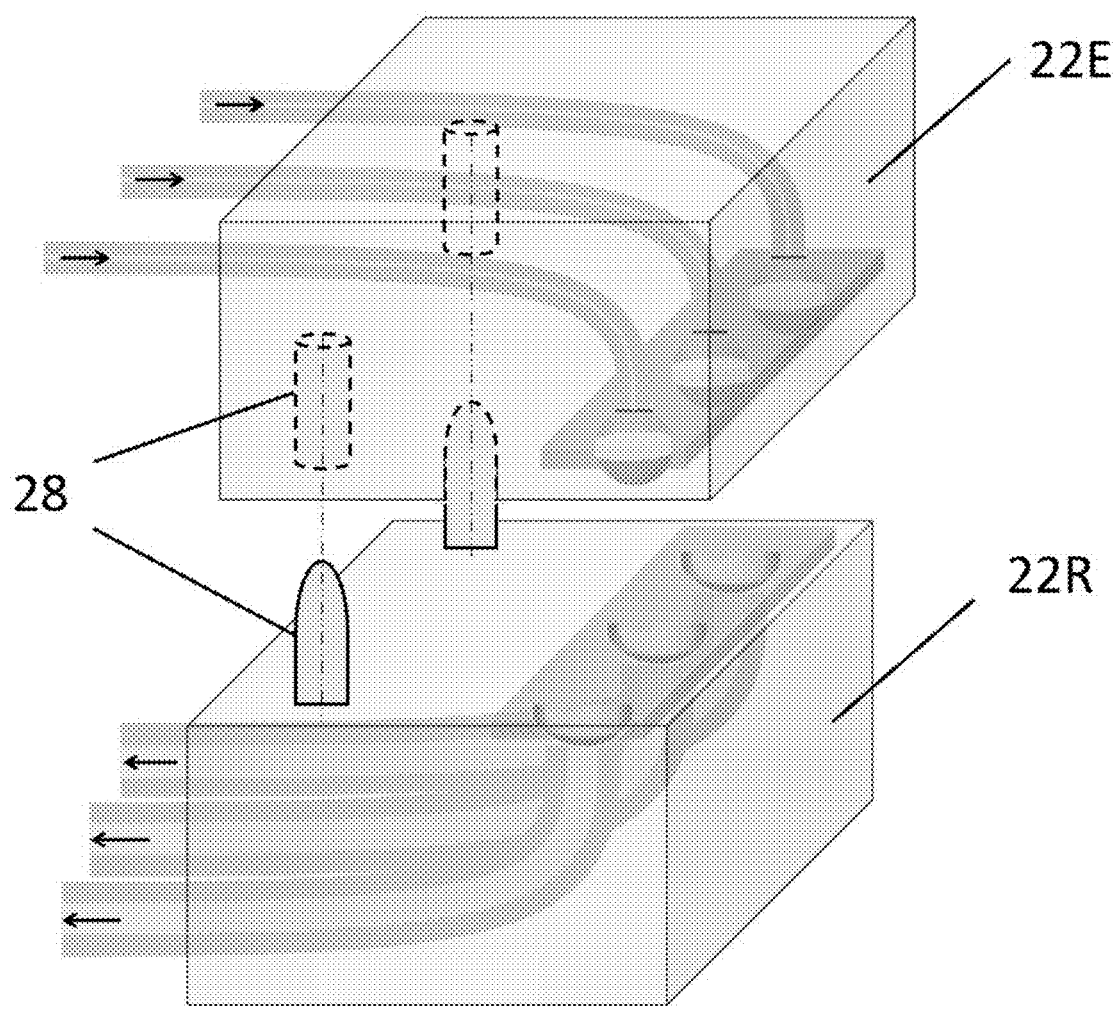
FIG. 11 illustrates the emitter block and receiver block of FIGS. 9 and 10 with the addition of alignment means for aligning the emitter and receiver blocks.
Figure 12A:
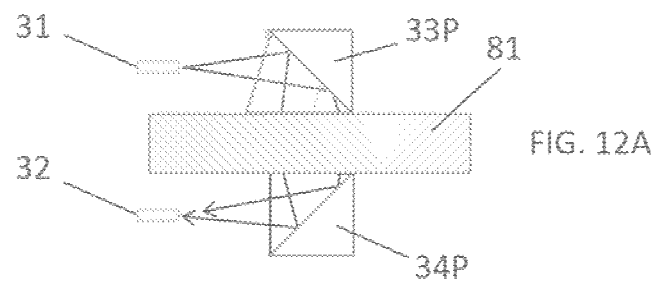
FIGS. 12A-12E provide examples of optical components and configurations to impose emitted light onto the test subject and collect emitted light from the opposite side of the test subject.
Figure 12B:
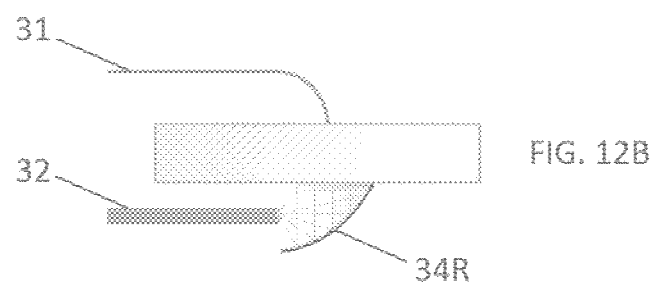
Figure 12C:
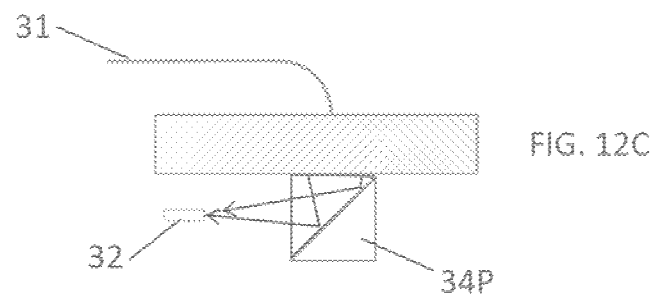
Figure 12D:
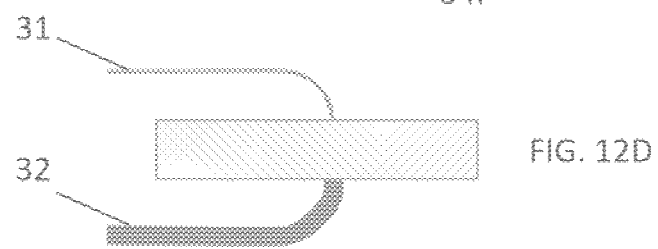
Figure 12E:
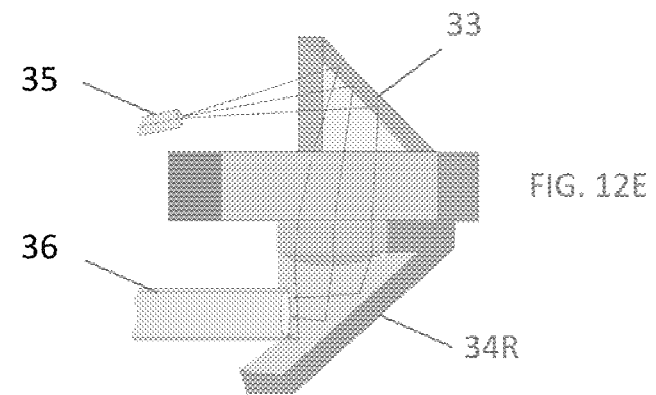

Optical enhancement methods may be employed to manage the delivery of emissive signals to the liquid sample. Such enhancement methods may include the use of a lens or lens system to further control the delivery of emissive signals and various techniques may be employed for aligning these individual lens or lens systems with the optical fiber or fibers, an illustrative example of which is illustrated in FIG. 9 in which three formed fibers are fed into emitter block 22E where ball lenses 33B are held in a carrier and an anti-reflective coating 25 is used. FIG. 10 illustrates how a receiver block 22R can be employed for aligning multiple receiving signals while FIG. 11 illustrates use of alignment means 28, one example of which is one or more registration pins, to insure correct alignment between the emissive optical fibers of emitter block 22E and the receiving optical fibers of receiver block 22R. FIGS. 12A-12E illustrate additional optical enhancement methods which may be employed to manage the delivery of emissive signals to the liquid sample. In FIG. 12A, the ends of the emissive and receiving optical fibers are distant from an optical element, such as an emitter prism 33P and a receiver prism 34P, which focus the emitting and receiving light beams, respectively. In FIG. 12B, the emitter optical fiber is flush against the liquid sample whereas a receiving optical element, an example of which is a reflector 34R, focuses light into the receiving optical fiber. In FIG. 12C, in contrast to FIG. 12B, a receiving prism 34P focuses light onto a receiver optical fiber physically distanced apart from receiving prism 34P. In FIG. 12E, emitter optical fiber emitter 35 is spaced physically apart from emitter optical element 33 which collects and focuses light into the liquid sample while receiver optical element 34 collects light and focuses it on receiver optical fiber receiver 36.

Figure 13A:
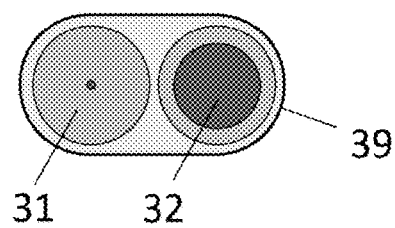
FIGS. 13A-13F are cross section illustrations of various optical cable configurations in accordance with the present invention.
Figure 13B:
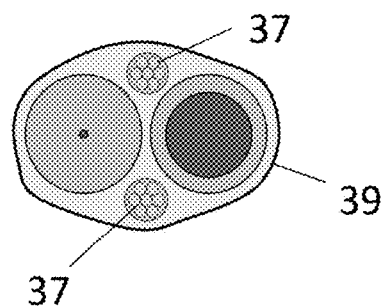
Figure 13C:
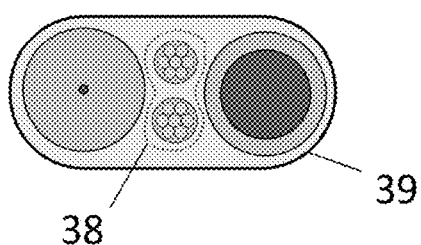
Figure 13D:
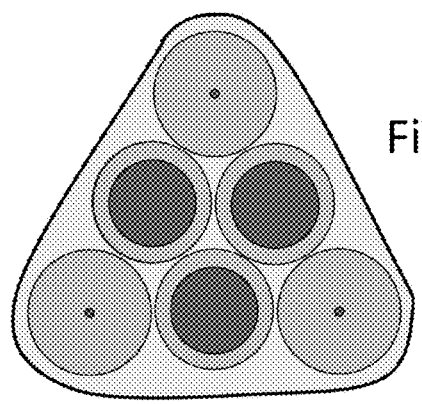
Figure 13E:
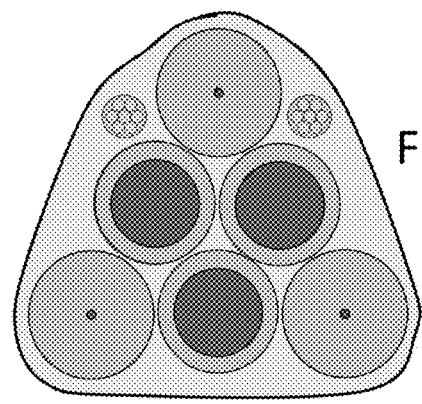
Figure 13F:
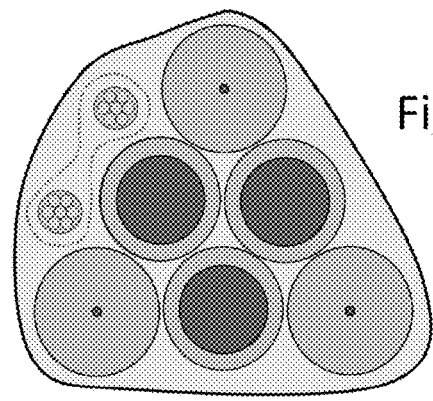

Optical cable 30 connects distal sensor module 20 to connector system 40 and includes single mode optical fibers and/or multimode optical fibers used to deliver optical emissions to the liquid sample and then to capture optical effects from the liquid sample. FIGS. 13A-13F illustrate some examples of cross sections of optical cable 30 with different constructions and purposes. In FIG. 13A, a single mode optical fiber 31 and a multimode optical fiber 32 are contained within cable jacket 39. In FIG. 13B, a single mode optical fiber 31, a multimode optical fiber 32 and two stranded electrical conductors 37 are contained within cable jacket 39. In FIG. 13C, a single mode optical fiber 31, a multimode optical fiber 32 and a braided shielding around electrical conductors 38 are contained within cable jacket 39. FIGS. 13D-13F are similar to FIGS. 13A-13C except that they each illustrate use of three single mode optical fibers 31 and three multimode optical fibers 32.

Figure 14:
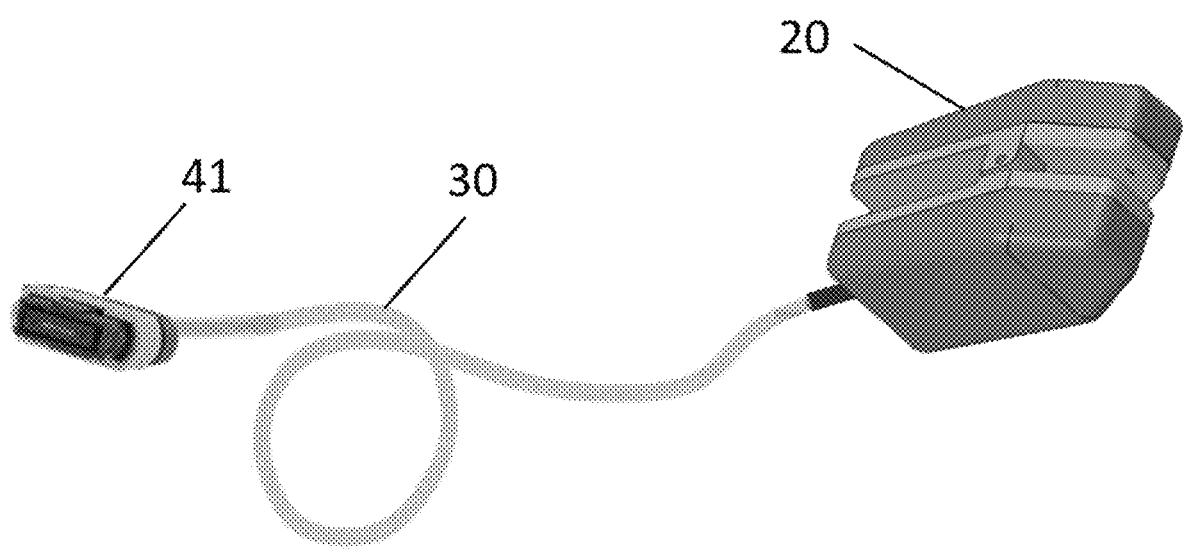
FIG. 14 illustrates a disposable component of an apparatus according to the present invention.

Connector system 40 is configured to allow distal sensor module 20 to be connected to and disconnected from controller 10. In an especially preferred embodiment, pluggable components of connector system 40 incorporate any variation of multiple fiber optic and electronic interfaces for delivering optical and electronic information to distal sensor module 20 and returning optical and electronic information from distal sensor module 20. A pluggable design incorporates suitable alignment features for mating of necessary interfaces and contacts and suitable retention features (examples of which include, but are not limited to, rotary locking methods, snap locking methods and latching locking methods) to ensure that during the period of use the mated pair remains properly connected. FIG. 14 illustrates distal sensor module 20 with optical cable 30 and one half 41 of a pluggable connector system 40. If desired, two halves 41 and 42 of a connector system 40 can be held together by a suitable connector retention means 44, examples of which might include tape or a clamp spring.

As already noted, it is especially preferred that distal sensor module 20 is configured to be held in place by a retention mechanism, to deliver controlled optical emissions to the liquid sample, and then to capture optical effects from the liquid sample. A convenient retention mechanism is a clamp. However, one problem with a clamp is that the pressure it applies can vary depending upon the size of the human body it is clamped to. It is important to have repeatability for accurate measurements, and simply using an uncontrolled clamping pressure will not necessarily provide reliable, repeatable, accurate test measurements. Another problem with a clamp is that a constant clamping pressure at a pressure which is higher than necessary to simply hold the clamp in place can interfere with normal interstitial fluid transfer in the skin testing region and, in particular, the perfusion of blood in the sample matrix.

To overcome problems arising from uncontrolled clamping pressure, the present invention requires that a liquid sample of the human body be established and maintained with a specified sample height by mechanical means during a test period. The "liquid sample" will not be completely liquid; rather, it is defined herein as a sample site which includes liquid as well as non-liquid substances, such as skin, vessels and other components found in a human body, or, in other words, solid and liquid components suspended in a sampling matrix within the human body. The goal of the clamping force is to compress the tissue investigative site to a fixed stop that provides the repeatability, reliability and accuracy necessary for target analyte measurement and establishes a fixed illumination zone and, even more particularly, to do so when the analyte being measured is glucose and the absorption band of glucose being monitored has center wavelength of 1,150 nm. In this regard, there is an ideal fixed stop for non-obese users (in the range of approximately 2 mm to approximately 4 mm fixed height between the optical emitter and the optical receiver) and for obese users (in the range of approximately 3 mm to approximately 6 mm fixed height between the optical emitter and the optical receiver).

Because the present invention is particularly well-suited for use in continuous monitoring, and especially well-suited for use in continuous monitoring in a controlled setting, such as where humans receive care in hospitals or other acute or chronic care facilities, it is especially desirable that distal sensor 20 be attached to a human body and connected to a remote controller 10 (either of which can be done first), and then a liquid sample be established in the human body with a specified sample height $H_c$ by mechanical means during a test period during which optical emissions are transmitted into the liquid sample and optical effects are captured from the liquid sample and then pressure is reduced on the liquid sample after the test period, while this process can be repeated over time while the distal sensor remains attached to the human body and connected to the remote controller. The results of such testing can be used to electronically calculate and output information about the concentration of the targeted analyte in the liquid sample of the human body through use of the captured optical effects, and such output information can be displayed when ready, meaning periodically, as well as stored and used to present output information about trends and historical results of such testing over a relevant period or periods of time.

One method of taking repetitive measurements with a distal sensor 20 without maintaining a constant pressure $H_c$ is to clamp the distal sensor module to the human patient through use of a clamping system configured to supply a first clamping pressure sufficient to maintain the distal sensor module clamped to the patient and then causing the distal sensor module to apply a second clamping pressure to the patient through use of the clamping system to maintain a specified sample height of the liquid sample (i.e., the skin testing region) during a test period so that during the test period optical emissions are transmitted into the liquid sample and optical effects are captured from the liquid sample while the second clamping pressure, which is greater than the first clamping pressure, is being applied, which also then allows the second clamping pressure to be reduced after the test period. It is also worth noting that while it is especially preferred that both clamping pressures be applied through the same physical clamping members, two separate systems will accomplish the same purpose and are within the contemplated scope of the present invention.

To better illustrate the present invention, especially preferred embodiments of a clamping system will now be described in even greater detail as illustrated in FIGS. 16 and 17A-17E. It should be understood that these are not the only embodiments or methods for creating two different pressures on the skin testing region, and these embodiments are not meant to be limiting of the present invention; rather, they are merely illustrative of concepts already described.

In these especially preferred embodiments clamping system 60 takes the form of a clamp having two clamp jaws, 61 and 62, a spring 63 and two handles, 64 and 65. Located between handles 64 and 65 is either a pneumatic-mechanical clamping means 72 or an electro-mechanical clamping means 73. FIG. 17A illustrates use of pressure bladder 66 which can be inflated or deflated via pneumatic line 69. When pressure bladder 66 is at a deflated pressure it occupies the area depicted as 68 whereas when pressure bladder is at an inflated pressure it occupies the area depicted as 67. Pneumatic line 69 feeds into optical cable 30 and is controlled by a controller 10. It is also especially preferred that clamping system 60 have the additional support of being held in place by the retentive mechanism of a thumb strap 71 threaded through slot 70. In FIG. 17B, a stepper motor 74 (also shown separately in FIG. 17C with its designated length of travel LT) has replaced the pneumatic-mechanical mechanism depicted in FIG. 17A, and FIGS. 17D and 17E illustrate a linear piezo actuator 75 and a linear piezo actuator with ratchet 76 which could replace stepper motor in FIG. 17B.

While it is especially preferred that clamping pressure not be maintained continuously to maintain the constant pressure $H_c$, it is possible that such pressure might be maintained continuously, such as by an adjustable fixed stop clamping mechanism, so long as the time during which such pressure is applied does not lead to physiological problems with the human patient in which it is being maintained. In this regard, it is worth stating again that the present invention is especially well-suited for measuring glucose at the glucose absorption band with center wavelength of 1,150 nm and the ideal fixed stop for non-obese users is in the range of approximately 2 mm to approximately 4 mm fixed height between the optical emitter and the optical receiver while the ideal fixed stop for obese users is in the range of approximately 3 mm to approximately 6 mm fixed height between the optical emitter and the optical receiver.

Figure 16:
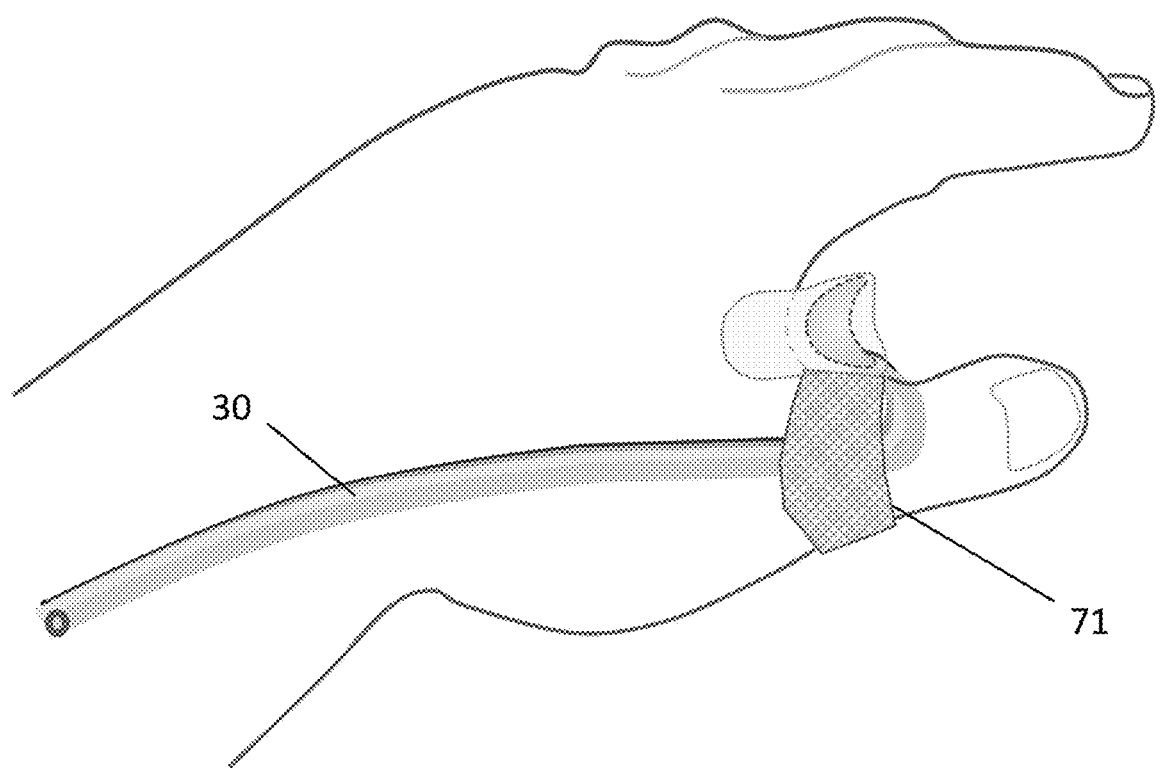
FIG. 16 illustrates a distal sensor module in accordance with the present invention which has been attached to a human thumb using a spring clamp.
Figure 18:
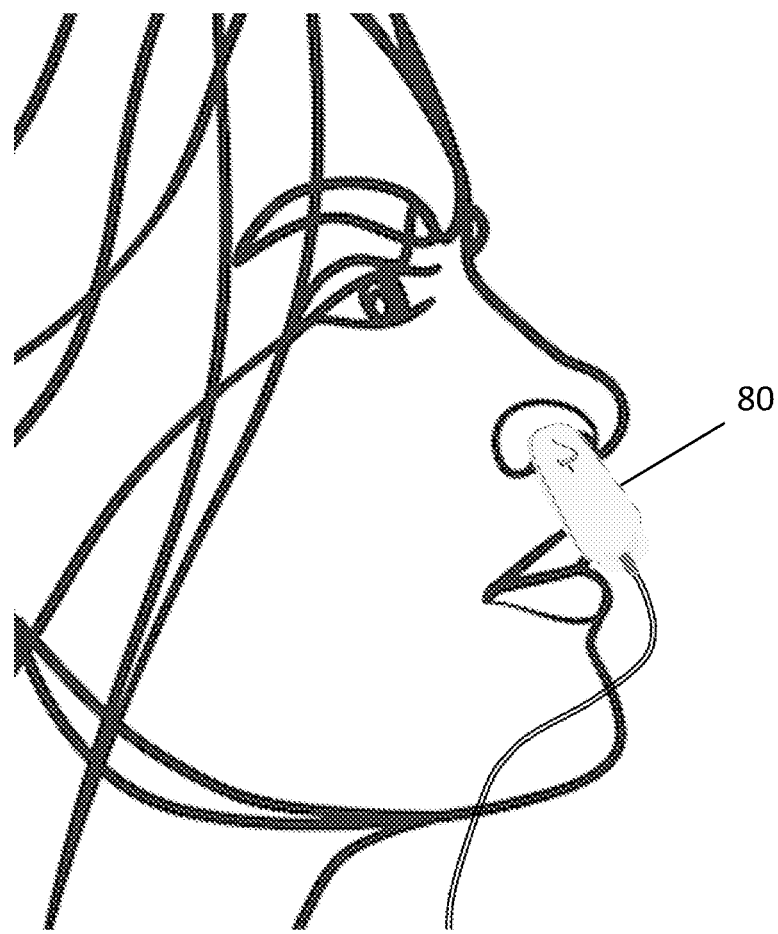
FIGS. 18, 19A, 19B, 20, 21 and 22 illustrate various ways in which a distal sensor module in accordance with the present invention can be attached to different parts of a human body.
Figure 19A:
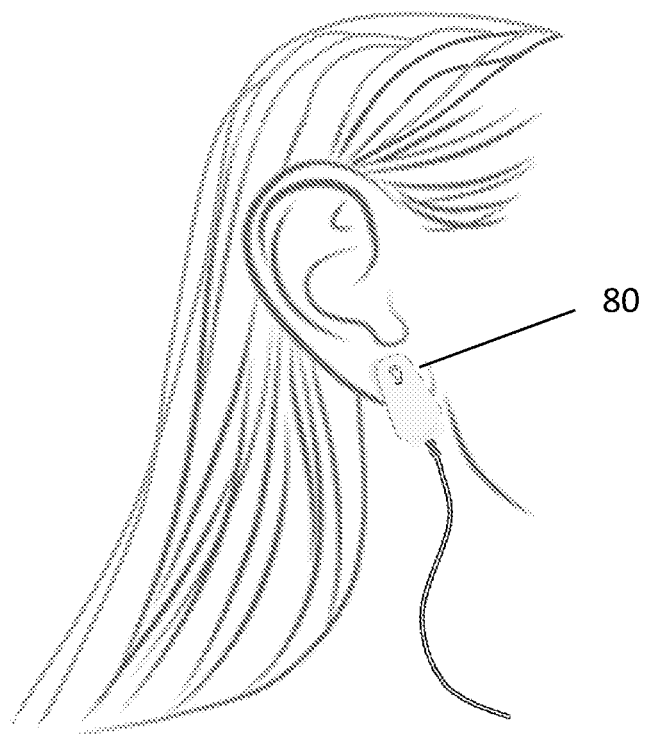
Figure 19B:
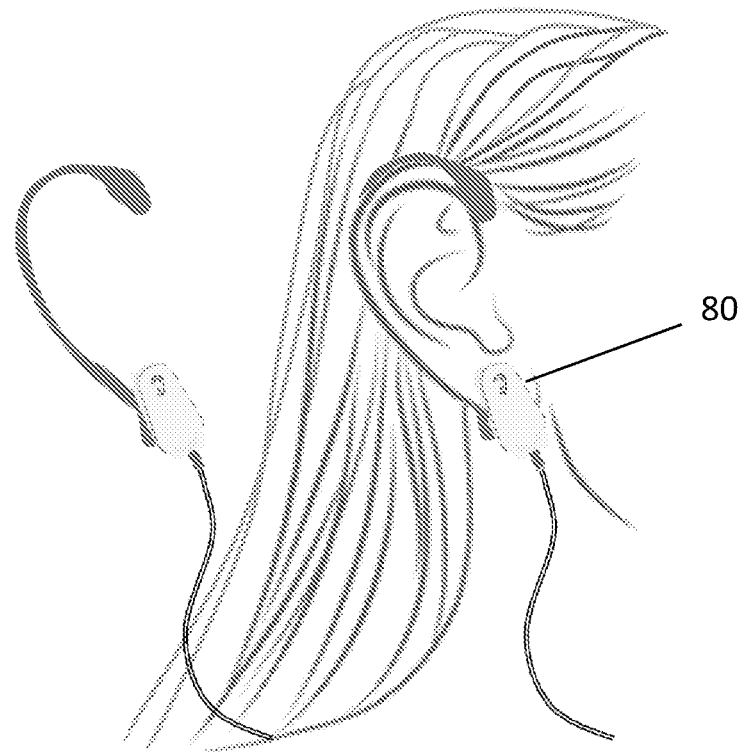
Figure 20:
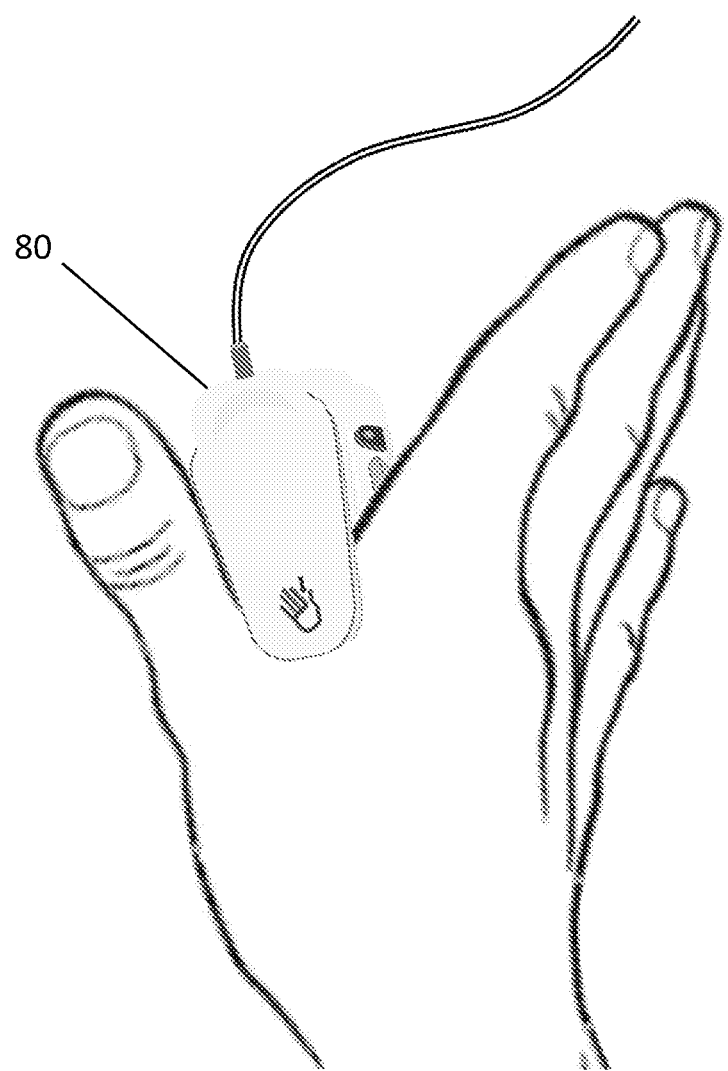
Figure 21:
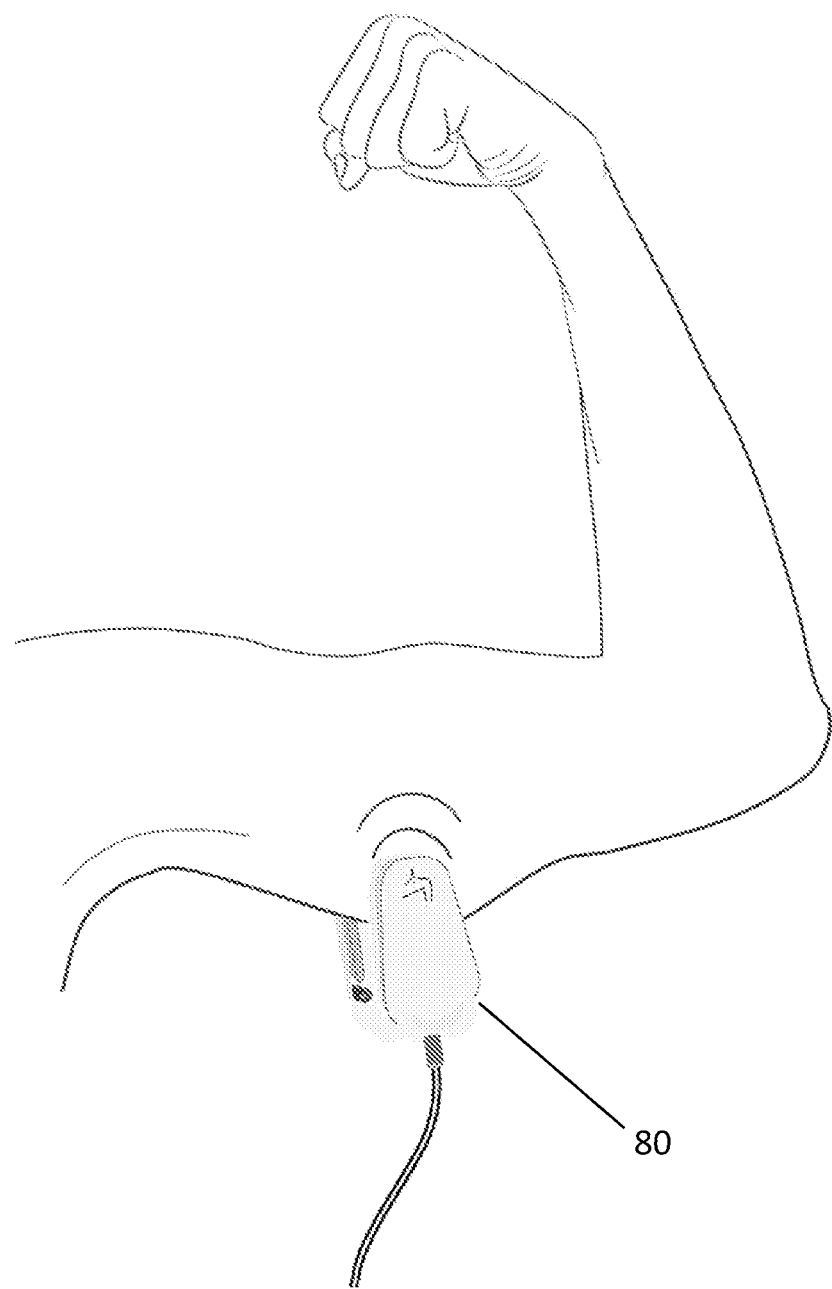
Figure 22:
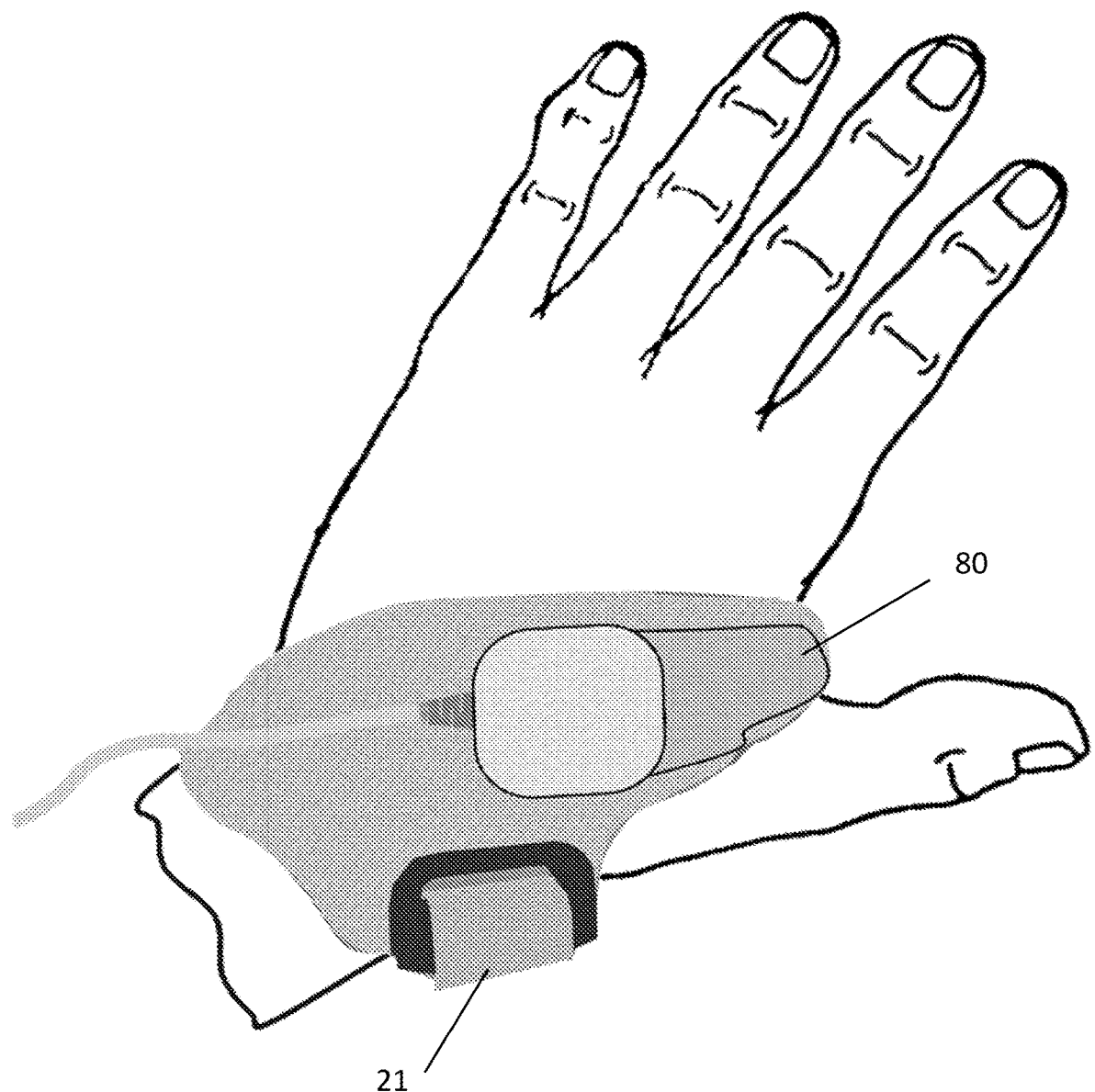

It is also worth noting that a distal sensor module in accordance with the present invention can be attached to human sample sites 80 in various parts of a human body, as is illustrated in FIGS. 18, 19A, 19B, 20, 21 and 22, and that straps and other mechanical devices, as is illustrated in FIGS. 19B and 22, can optionally be used as retention mechanisms 21 to assist retaining the distal sensor module (as was the case in FIG. 16). Note that in all such locations the ideal fixed stops noted for non-obese and obese users can readily be obtained.

Figure 24:
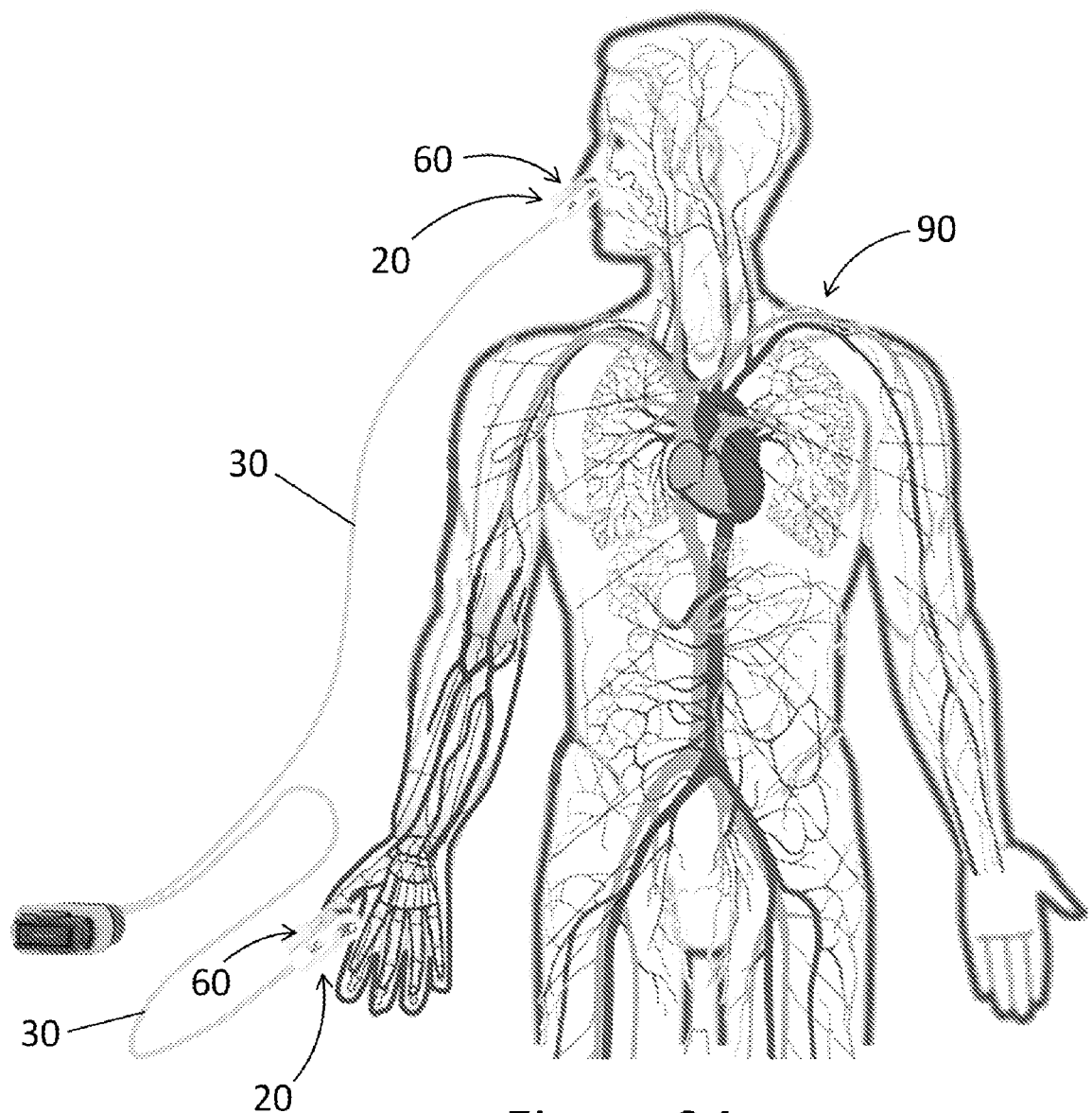
FIG. 24 illustrates the use of two distal sensor modules which feed into a common connector for connection with a controller in accordance with the present invention.

Finally, it is also worth noting that more than one distal sensor module can be attached to controller 10; multiple distal sensor modules can be attached through separate connector systems 40 or, as is the case illustrated in FIG. 24, be attached through a common connector system. The use of multiple distal sensor modules opens up a number of possibilities of study, to see how measurements may vary depending upon the measuring sites in a body, and it is believed that measurement in a foot, and especially the region of the toes, such as webbing between toes, when compared to measurements of other sites in a body (e.g., the ear or nose), might help to identify, diagnose and possibly improve treatment of diabetic neuropathy. The same can be said for diabetic neuropathy in hands. It is believed the key here is that measurement of blood glucose levels in areas where the walls of the small blood vessels (capillaries) have been damaged may identify a different blood glucose level than in healthy body tissue and this difference can be used to identify, diagnose and possibly improve treatment.

Although the foregoing detailed description is illustrative of preferred embodiments of the present invention, it is to be understood that additional embodiments thereof will be obvious to those skilled in the art. Further modifications are also possible in alternative embodiments without departing from the inventive concept.

Accordingly, it will be readily apparent to those skilled in the art that still further changes and modifications in the actual concepts described herein can readily be made without departing from the spirit and scope of the disclosed inventions.

What is claimed is:

1. An apparatus, comprising:
   a controller configured to deliver controlled optical emissions to a liquid sample being tested in a human body, to capture desired optical data returned from the liquid sample, and to electronically calculate a concentration measurement of a targeted analyte in the liquid sample through use of a preselected algorithm with the captured optical data;
   a distal sensor module configured to be held in place by a retention mechanism, to deliver controlled optical emissions to the liquid sample, and then to capture optical effects from the liquid sample;
   a second distal sensor module configured to be held in place by a second retention mechanism, to deliver controlled optical emission to a second liquid sample being tested in the human body, and then to capture optical effects from the liquid sample;
   a clamping system configured to apply clamping pressure to the liquid sample to maintain a specified sample height of the liquid sample during a test period;
   a second clamping system configured to apply a second clamping pressure to the second liquid sample to maintain a second specified sample height of the second liquid sample during the test period;
   an optical cable configured to transmit controlled optical emissions from the controller to the distal sensor module and then to return captured optical effects from the distal sensor module to the controller;
   a second optical cable configured to transmit controlled optical emissions from the controller to the second distal sensor module and then to return captured optical effects from the second distal module to the controller;
   a connector system configured to allow the distal sensor module to be connected to and disconnected from the controller; and an information interface configured to output the concentration measurement.

2. The apparatus of claim 1, wherein the distal sensor is configured to apply a first clamping pressure which is sufficient to maintain the distal sensor module clamped to the human body and the clamping system is configured to apply a second clamping pressure to the liquid sample to maintain the specified sample height of the liquid sample during the test period, wherein the second clamping pressure is greater than the first clamping pressure.

3. The apparatus of claim 1, wherein the clamping system is configured so that it only applies pressure during a preselected time frame which includes a sample time period during the test period.

4. The apparatus of claim 3, wherein the clamping system utilizes a pneumatic-mechanical clamping means to generate a clamping force.

5. The apparatus of claim 3, wherein the clamping system utilizes an electro-mechanical clamping means to generate a clamping force.

6. The apparatus of claim 1, where the clamping system applies a preselected clamping pressure.

7. The apparatus of claim 1, wherein the connector system is comprised of:
alignment means for mating interfaces and contacts; and
retention means for ensuring the alignment means remains properly connected during the test period.

8. The apparatus of claim 1, wherein the distal sensor module is comprised of:
a single mode optical fiber emitter; and
a multimode optical fiber receiver.

9. The apparatus of claim 1, wherein the distal sensor module is comprised of:
at least one optical fiber emitter; and
at least one optical fiber receiver.

10. The apparatus of claim 9, further comprised of:
an emitter optical element at an emitter distal end with at least one optical fiber emitter configured to direct controlled emissions to the liquid sample; and
a receiver optical element at a receiver distal end with at least one optical fiber receiver configured to receive optical effects from the liquid sample being tested.

11. The apparatus of claim 10, wherein the emitter optical element is aligned with the at least one optical fiber emitter and the receiver optical element is aligned with the at least one optical fiber receiver.

12. The apparatus of claim 10, wherein the emitter optical element is configured with at least one optical fiber emitter and the receiver optical element is configured with at least one optical fiber receiver.

13. The apparatus of claim 1, wherein the controller electronically calculates a second concentration measurement of the targeted analyte in the second liquid sample through use of the preselected algorithm with the captured optical data from the second distal sensor.

14. A method of non-invasively ascertaining concentration of a targeted analyte in a human body, comprising the steps of:
Step 1: attaching a distal sensor to a human body and connecting the distal sensor to a remote controller;
Step 2: establishing and maintaining a liquid sample of the human body with a specified sample height by mechanical means during a test period;
Step 3: transmitting optical emissions into the liquid sample during the test period;
Step 4: capturing optical effects from the liquid sample during the test period;
Step 5: reducing pressure on the liquid sample after the test period; and
repeating Step 2 through Step 5 at least once while the distal sensor remains attached to the human body and connected to the remote controller;
Step 1A: attaching a second distal sensor to the human body and connecting the second distal sensor to the remote controller;
Step 2A: establishing and maintaining a second liquid sample of the human body with the specified sample height by second mechanical means during the test period;
Step 3A: transmitting optical emissions into the second liquid sample during the test period;
Step 4A: capturing second optical effects from the second liquid sample during the test period;
Step 5A: reducing pressure on the second liquid sample after the test period; and
repeating Steps 2A through Step 5A at least once while the second distal sensor remains attached to the human body and connected to the remote controller.

15. The method of claim 14, wherein the distal sensor and the second distal sensor are attached to different parts of the human body.

16. The method of claim 15, further comprising electronically calculating information about the concentration of the targeted analyte in the liquid sample and the second liquid sample through use of the captured optical effects the second captured optical effects and a preselected algorithm.

* * * * *